United States Patent [19]
Gruss et al.

[11] Patent Number: 6,028,184
[45] Date of Patent: Feb. 22, 2000

[54] PAX6 AND PAX4 NUCLEIC ACID MIXTURES

[75] Inventors: Peter Gruss; Luc St.-Onge, both of Göttingen, Germany

[73] Assignee: Max-Plank-Gesellschaft zur Forderung der Wissenschaften e.V., Berlin, Germany

[21] Appl. No.: 08/778,394

[22] Filed: Dec. 31, 1996

[51] Int. Cl.[7] .......................... C07H 21/02; C07H 21/04; C12N 5/10; C12N 15/70
[52] U.S. Cl. ............................ 536/23.1; 536/24.3; 435/6; 435/240.2; 435/320.1; 514/44
[58] Field of Search .................................. 536/23.1, 24.3; 435/320.1, 240.2; 514/44

[56] References Cited
PUBLICATIONS

Walther et al. Development 113:1435–1450, 1991.
Correll et al. Human Gene Therapy 1: 277–287, 1990.
Paillard, Human Gene Therapy 8:2009–2010, 1997.
Orkin, Report and Recommendations of the Panel to Assess the NIH Investment in Research on Gene Therapy, 1995.

*Primary Examiner*—Jeffrey Fredman
*Attorney, Agent, or Firm*—Frommer Lawrence & Haug LLP; Thomas J. Kowalski

[57] ABSTRACT

The present invention relates to a novel method for testing the developmental status in pancreatic cells of a mammal. The present invention further relates to applications in the medical field that directly arise from the method of the invention. Additionally, the present invention relates to transgenic mammals comprising at least one inactivated Pax6 allele and optionally at least one inactivated Pax4 allele.

4 Claims, 60 Drawing Sheets

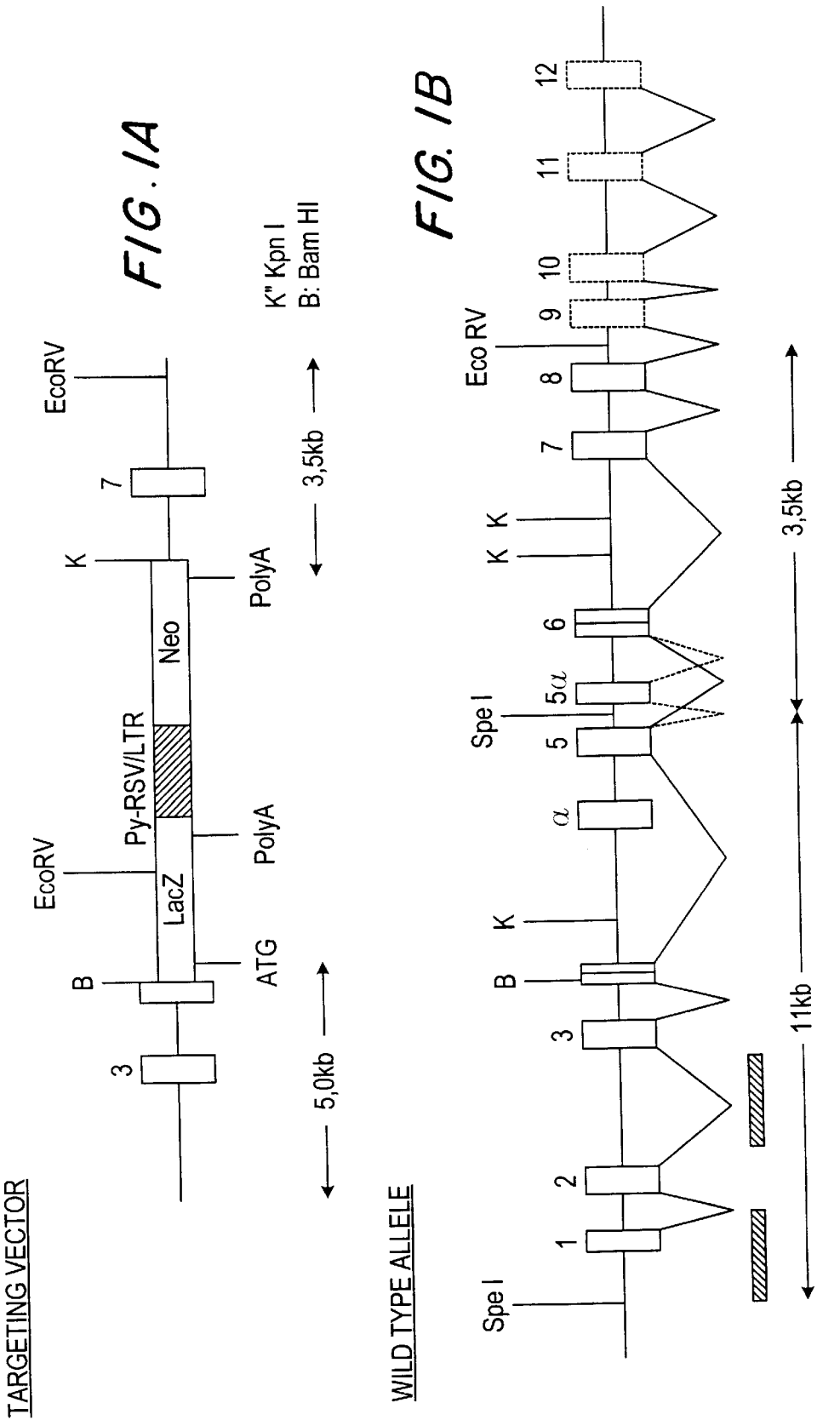

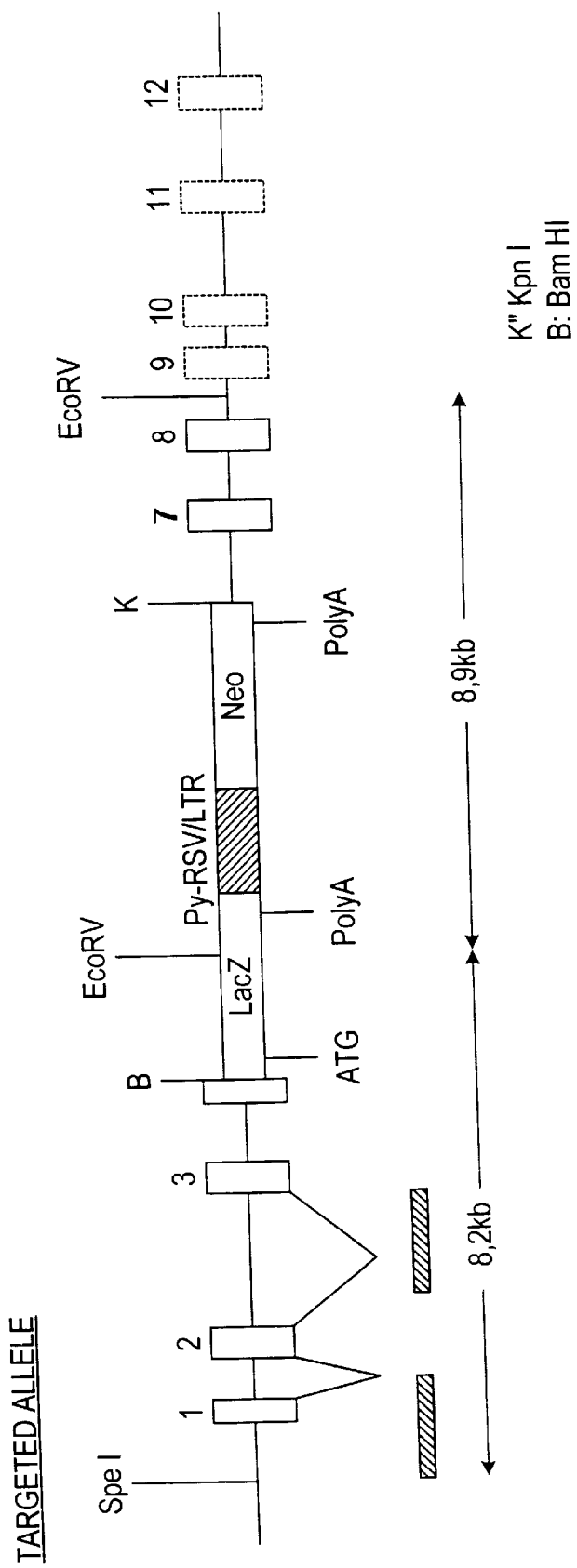
FIG. IC

Insulin

Insulin

Glucagon

Glucagon

Glucagon

Glucagon

FIG. 6A
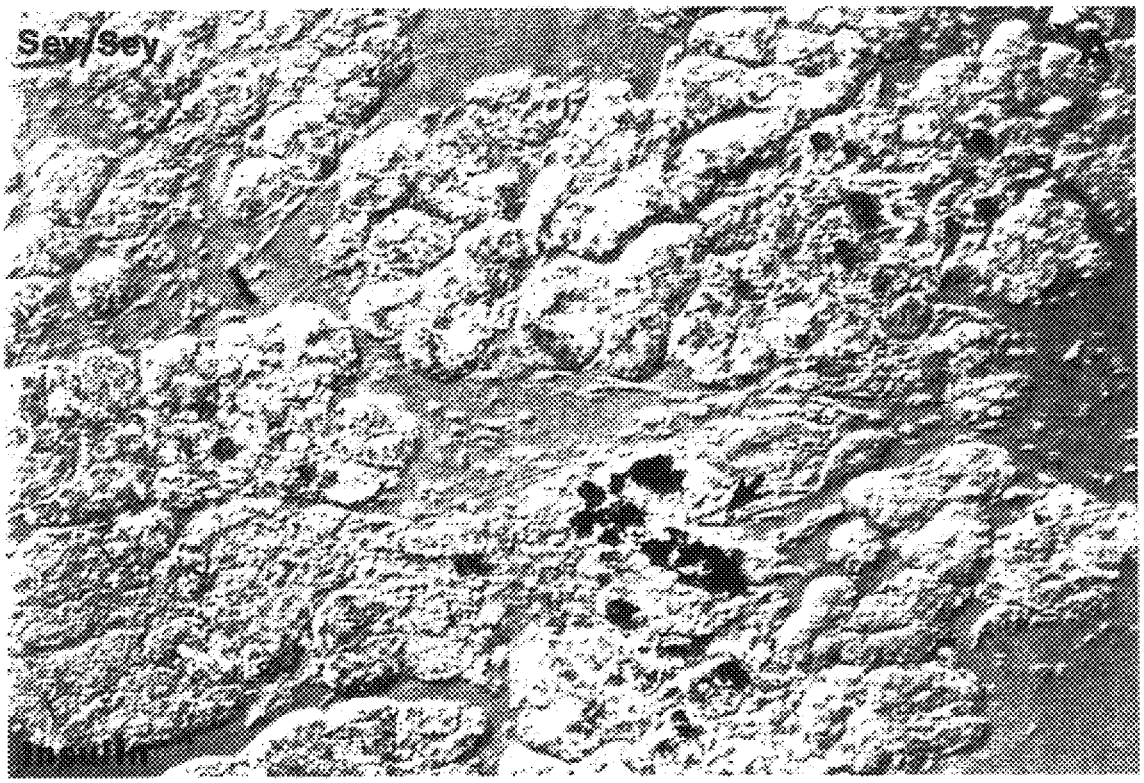
FIG. 6B

FIG. 7A
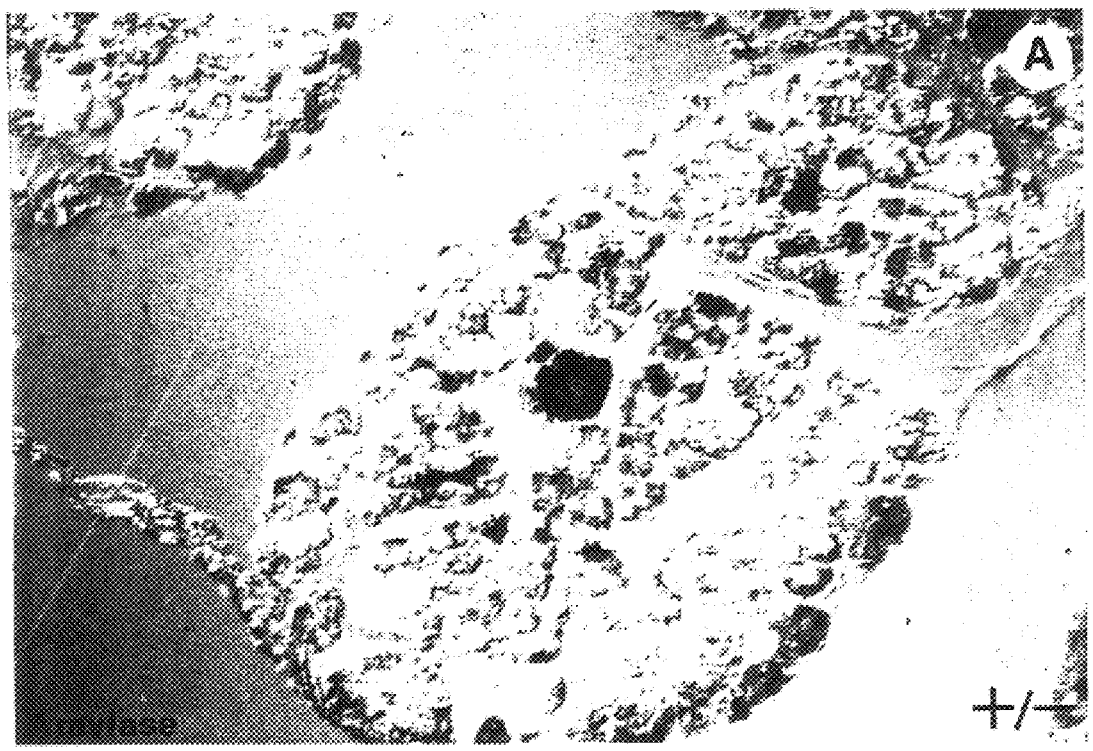
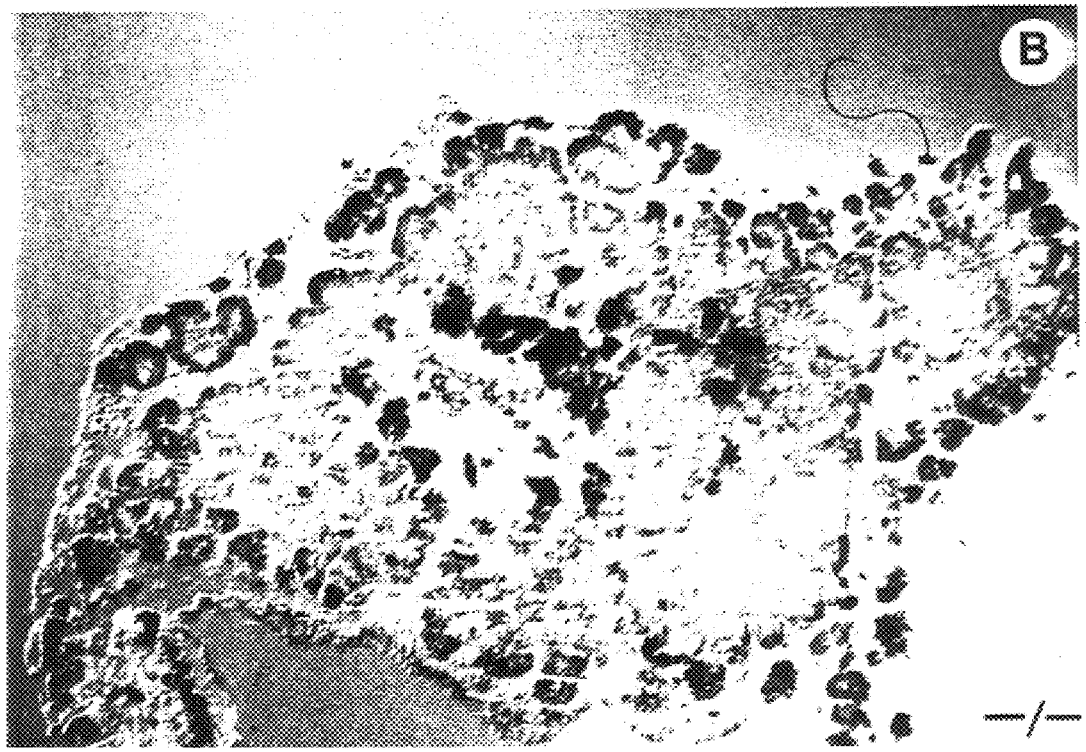
FIG. 7A

FIG.10A (1) GENERAL INFORMATION:

(iii) NUMBER OF SEQUENCES: 4

(2) INFORMATION FOR SEQ ID NO: 1:

(i) SEQUENCE CHARACTERESTICS:

(A) LENGTH: 2481 base pairs (B) TYPE: nucleic acid (C) STRANDEDNESS: single (D) TOPOLOGY: linear (ii) MOLECULE TYPE: other nucleic acid (xi) SEQUENCE DESCRIPTION : SEQ ID NO: 1:

```
ACA ACG ACG AAA GAG AGG ATG CCT CTT AAA GGC AGA AGA CTT TAA CCA AGG GCG    54
GTG AGC AGA TGT GTG AGA TCT TCT ATT CTA GAA GTG GAC GTA TAT CCC AGT TCT CAG AGC   114
CCC GTA TTC GAG CCC CGT GGG ATC CGG AGG CTG CCA ACC AGC TCC AGC ATG CAG AAC AGT   174
                                                                Met Gln Asn Ser
                                                                 1
```

```
CAC AGC GGA GTG AAT CAG CTT GGT GGT GTC TTT GTC AAC GGG CGG CCA CTG CCG GAC TCC    234
His Ser Gly Val Asn Gln Leu Gly Gly Val Phe Val Asn Gly Arg Pro Leu Pro Asp Ser
  5                  10                  15                  20

ACC CGG CAG AAG ATC GTA GAG CTA GCT CAC AGC GGG GCC CGG CCG TGC GAC ATT TCC CGA    294
Thr Arg Gln Lys Ile Val Glu Leu Ala His Ser Gly Ala Arg Pro Cys Asp Ile Ser Arg
         25                  30                  35                  40

ATT CTG CAG ACC CAT GCA GAT GCA AAA GTC CAG GTG CTG GAC AAT GAA AAC GTA TCC AAC    354
Ile Leu Gln Thr His Ala Asp Ala Lys Val Gln Val Leu Asp Asn Glu Asn Val Ser Asn
             45                  50                  55                  60

GGT TGT GTG AGT AAA ATT CTG GGC AGG TAT TAC GAG ACT GGC TCC ATC AGA CCC AGG GCA    414
Gly Cys Val Ser Lys Ile Leu Gly Arg Tyr Tyr Glu Thr Gly Ser Ile Arg Pro Arg Ala
     65                  70                  75                  80

ATC GGA GGG AGT AAG CCA AGA GTG GCG ACT CCA GAA GTT GTA AGC AAA ATA GCC CAG TAT    474
Ile Gly Gly Ser Lys Pro Arg Val Ala Thr Pro Glu Val Val Ser Lys Ile Ala Gln Tyr
         85                  90                  95                 100

AAA CGG GAG TGC CCT TCC ATC TTT GCT TGG GAA ATC CGA GAC AGA TTA TCC GAG GGG        534
Lys Arg Glu Cys Pro Ser Ile Phe Ala Trp Glu Ile Arg Asp Arg Leu Ser Glu Gly
            105                 110                 115                 120
```

FIG. 10B

```
GTC TGT ACC AAC GAT AAC ATA CCC AGT GTG TCA TCA ATA AAC AGA GTT CTT CGC AAC CTG    594
Val Cys Thr Asn Asp Asn Ile Pro Ser Val Ser Ser Ile Asn Arg Val Leu Arg Asn Leu
125                     130                 135                 140

GCT AGC GAA AAG CAA CAG ATG GGC GCA GAC GGC ATG TAT GAT AAA CTA AGG ATG TTG AAC    654
Ala Ser Glu Lys Gln Gln Met Gly Ala Asp Gly Met Tyr Asp Lys Leu Arg Met Leu Asn
145                 150                 155                 160

GGA AGC TGG GGC ACA CGC CCT GGT TGG TAT CCC GGG ACT TCA GTA CCA GGG    714
Gly Ser Trp Gly Thr Arg Pro Gly Trp Tyr Pro Gly Thr Ser Val Pro Gly
165                 170                 175                 180

CAA CCC ACG CAA GAT GGC TGC CAG CAA CAG GAA GGA GGG GGA GAG AAC ACC AAC TCC ATC    774
Gln Pro Thr Gln Asp Gly Cys Gln Gln Gln Glu Gly Gly Gly Glu Asn Thr Asn Ser Ile
185                 190                 195                 200

AGT TCT AAC GGA GAA GAC TCG GAT GAA GCT CAG ATG CGA CTT CAG CTG AAG CGG AAG CTG    834
Ser Ser Asn Gly Glu Asp Ser Asp Glu Ala Gln Met Arg Leu Gln Leu Lys Arg Lys Leu
205                 210                 215                 220

CAA AGA AAT AGA ACA TCT TTT ACC CAA GAG CAG ATT GAG GCT CTG GAG AAA GAG TTT GAG    894
Gln Arg Asn Arg Thr Ser Phe Thr Gln Glu Gln Ile Glu Ala Leu Glu Lys Glu Phe Glu
225                 230                 235                 240
```

FIG. 10C

```
AGG ACC CAT TAT CCA GAT GTG TTT GCC CGG GAA AGA CTA GCA GCC AAA ATA GAT CTA CCT    954
Arg Thr His Tyr Pro Asp Val Phe Ala Arg Glu Arg Leu Ala Ala Lys Ile Asp Leu Pro
245                     250                     255                     260

GAA GCA AGA ATA CAG GTA TGG TTT TCT AAT CGA AGG GCC AAA TGG AGA AGA GAA GAG AAA   1014
Glu Ala Arg Ile Gln Val Trp Phe Ser Asn Arg Arg Ala Lys Trp Arg Arg Glu Glu Lys
265                     270                     275                     280

CTG AGG AAC CAG AGA AGA CAG GCC AGC AAC ACT CCT AGT CAC ATT CCT ATC AGC AGC AGC   1074
Leu Arg Asn Gln Arg Arg Gln Ala Ser Asn Thr Pro Ser His Ile Pro Ile Ser Ser Ser
285                     290                     295                     300

TTC AGT ACC AGT GTC TAC CAG CCA ATC CCA CAG CCC ACA CCT GTC TCC TCC TTC ACA       1134
Phe Ser Thr Ser Val Tyr Gln Pro Ile Pro Gln Pro Thr Pro Val Ser Ser Phe Thr
305                     310                     315                     320

TCA GGT TCC ATG TTG GGC CGA ACA GAC ACC GCC CTC ACC AAC ACG TAC AGT GCT TTG CCA   1194
Ser Gly Ser Met Leu Gly Arg Thr Asp Thr Ala Leu Thr Asn Thr Tyr Ser Ala Leu Pro
325                     330                     335                     340

CCC ATG CCC AGC TTC ACC ATG GCA AAC AAC CTG CCT ATG CAA CCC CCA GTC CCC AGT CAG   1254
Pro Met Pro Ser Phe Thr Met Ala Asn Asn Leu Pro Met Gln Pro Pro Val Pro Ser Gln
345                     350                     355                     360
```

*FIG. 10D*

```
ACC TCC TCA TAC TCG TGC ATG CTG CCC ACC AGC CCG TCA GTG AAT GGG CGG AGT TAT GAT   1314
Thr Ser Ser Tyr Ser Cys Met Leu Pro Thr Ser Pro Ser Val Asn Gly Arg Ser Tyr Asp
365                 370                 375                 380

ACC TAC ACC CCT CCG CAC ATG CAA ACA CAC ATG AAC AGT CAG CCC ATG GGC ACC TCG GGG   1374
Thr Tyr Thr Pro Pro His Met Gln Thr His Met Asn Ser Gln Pro Met Gly Thr Ser Gly
        385                 390                 395                 400

ACC ACT TCA ACA GGA CTC ATT TCA CCT GGA GTG TCA GTT CCC GTC CAA GTT CCC GGG AGT   1434
Thr Thr Ser Thr Gly Leu Ile Ser Pro Gly Val Ser Val Pro Val Gln Val Pro Gly Ser
405                 410                 415                 420

GAA CCT GAC ATG TCT CAG TAC TGG CCT CGA TTA CAG TAA AGA GAG AAG GAG AGA GCA TGT   1494
Glu Pro Asp Met Ser Gln Tyr Trp Pro Arg Leu Gln
425                 430                 435

GAT CGA GAG AGG AAA TTG TGT TCA CTC TGC CAA TGA CTA TGT GGA CAC AGC AGT TGG GTA   1554

TTC AGG AAA GAA AGA GAA ATG GCG GTT AGA AGC ACT TCA CTT TGT AAC TGT CCT GAA CTG   1614

GAG CCC GGG AAT GGA CTA GAA CCA AGG ACC TTG CGT ACA GAA GGC ACG GTA TCA GTT GGA   1674

ACA AAT CTT CAT TTT GGT ATC CAA ACT TTT ATT CAT TTT GGT GTA TTA TTT GTA AAT GGG   1734
```

FIG. 10E

```
CAT TGG TAT GTT ATA ATG AAG AAA AGA ACA ACA CAG GCT GTT GGA TCG CGG ATC TGT GTT  1794
GCT CAT GTG GTT GTT TAA AGG AAA CCA TGA TCG ACA AGA TTT GCC ATG GAT TTA AGA GTT  1854
TTA TCA AGA TAT ATC AAA TAC TTC TCC CCA TCT GTT CAT AGT TTA TGG ACT GAT GTT CCA  1914
AGT TTG TAT CAT TCC TTT GCA TAT AAT TGA ACC TGG GAC AAC ACA CAC TAG ATA TAT GTA  1974
AAA ACT ATC TGT TGG TTT TCC AAA GGT TGT TAA CAG ATG AAG TTT ATG TGC AAA AAA GGG  2034
TAA GAT ATG AAT TCA AGG AGA AGT TGA TAG CTA AAA GGT AGA GTG TGT CTT CGA TAT AAT  2094
ACA ATT TGT TTT ATG TCA AAA TGT AAG TAT TTG TCT TCC CTA GAA ATC CTC AGA ATG ATT  2154
TCT ATA ATA AAG TTA ATT TCA TTT ATA TTT GAC AAG AAT ACT CTA TAG ATG TTT TAT ACA  2214
CAT TTT CAT GCA ATC ATT TGT TTC TTT CTT GGC CAG CAA AAG TTA ATT GTT CTT AGA TAT  2274
AGC TGT ATT ACT GTT CAC AGT CCA ATC ATT TGC ATC TAG AAT TCA TTC CTA ATC AAT      2334
TAA AAG TGC TTG CAA GAG TTT TAA GTG TTT TGC AGT TGT TCA CAA ATA CAT ATC          2394
AAA ATT AAC CAT TGT TGA TTG TAA AAA AAC CAT GCC AAA GCC TTT GTA TTT TCT TTA      2454
TTA CCC TTG ACC GTA AGA CAT GAA TTC  2481
```

FIG. 10F

FIG. 11A (2) INFORMATION FOR SEQ ID NO: 2:

(i) SEQUENCE CHARACTERESTICS:

(A) LENGTH: 436 amino acids
    (B) TYPE: amino acid
    (D) TOPOLOGY: linear (ii) MOLECULE TYPE: protein (xi) SEQUENCE DESCRIPTION : SEQ ID NO: 2:

```
Met Gln Asn Ser His Ser Gly Val Asn Gln Leu Gly Gly Val Phe Val Asn Gly Arg Pro
 1                   5                  10                  15                  20
Leu Pro Asp Ser Thr Arg Gln Lys Ile Val Glu Leu Ala His Ser Gly Ala Arg Pro Cys
                        25                  30                  35                  40
Asp Ile Ser Arg Ile Leu Gln Thr His Ala Asp Ala Lys Val Gln Val Leu Asp Asn Glu
                        45                  50                  55                  60
Asn Val Ser Asn Gly Cys Val Ser Lys Ile Leu Gly Arg Tyr Tyr Glu Thr Gly Ser Ile
                        65                  70                  75                  80
Arg Pro Arg Ala
```

```
Ile Gly Gly Ser Lys Pro Arg Val Ala Thr Pro Glu Val Val Ser Lys Ile Ala Gln Tyr
85                  90                  95                  100

Lys Arg Glu Cys Pro Ser Ile Phe Ala Trp Glu Ile Arg Asp Arg Leu Leu Ser Glu Gly
        105                 110                 115                 120

Val Cys Thr Asn Asp Asn Ile Pro Ser Val Ser Ser Ile Asn Arg Val Leu Arg Asn Leu
        125                 130                 135                 140

Ala Ser Glu Lys Gln Met Gly Ala Asp Gly Met Tyr Asp Lys Leu Arg Met Leu Asn
        145                 150                 155                 160

Gly Gln Thr Gly Ser Trp Gly Thr Arg Pro Gly Trp Tyr Pro Gly Thr Ser Val Pro Gly
165                 170                 175                 180

Gln Pro Thr Gln Asp Gly Cys Gln Gln Glu Gly Gly Glu Asn Thr Asn Ser Ile
        185                 190                 195                 200

Ser Ser Asn Gly Glu Asp Ser Asp Glu Ala Gln Met Arg Leu Gln Leu Lys Arg Lys Leu
        205                 210                 215                 220

Gln Arg Asn Arg Thr Ser Phe Thr Gln Glu Gln Ile Glu Ala Leu Glu Lys Glu Phe Glu
        225                 230                 235                 240

Arg Thr His Tyr Pro Asp Val Phe Ala Arg Glu Arg Leu Ala Ala Lys Ile Asp Leu Pro
245                 250                 255                 260
```

*FIG. IIB*

```
Glu Ala Arg Ile Gln Val Trp Phe Ser Asn Arg Arg Ala Lys Trp Arg Arg Glu Glu Lys
265                 270                 275                 280
Leu Arg Asn Gln Arg Arg Gln Ala Ser Asn Thr Pro Ser His Ile Pro Ile Ser Ser Ser
285                 290                 295                 300
Phe Ser Thr Ser Val Tyr Gln Pro Ile Pro Gln Pro Thr Thr Pro Val Ser Ser Phe Thr
305                 310                 315                 320
Ser Gly Ser Met Leu Gly Arg Thr Asp Thr Ala Leu Thr Asn Thr Tyr Ser Ala Leu Pro
325                 330                 335                 340
Pro Met Pro Ser Phe Thr Met Ala Asn Asn Leu Pro Met Gln Pro Pro Val Pro Ser Gln
345                 350                 355                 360
Thr Ser Ser Tyr Ser Cys Met Leu Pro Thr Ser Pro Ser Val Asn Gly Arg Ser Tyr Asp
365                 370                 375                 380
Thr Tyr Thr Pro Pro His Met Gln Thr His Met Asn Ser Gln Pro Met Gly Thr Ser Gly
385                 390                 395                 400
Thr Thr Ser Thr Gly Leu Ile Ser Pro Gly Val Ser Val Pro Val Gln Val Pro Gly Ser
405                 410                 415                 420
Glu Pro Asp Met Ser Gln Tyr Trp Pro Arg Leu Gln
425                 430                 435
```

*FIG. IIC*

FIG. 12A (2) INFORMATION FOR SEQ ID NO: 3:

(i) SEQUENCE CHARACTERESTICS:

(A) LENGTH: 1275 base pairs (B) TYPE: nucleic acid (C) STRANDEDNESS: single (D) TOPOLOGY: linear (ii) MOLECULE TYPE: other nucleic acid (xi) SEQUENCE DESCRIPTION : SEQ ID NO: 3:

```
ACC AGC AAC CCT GGA GCC TGC ACA GAC CCT GAG ACC TCT TCC TGA ATT CCC ACC    54
TTT TTT CCT CCA TCC AGT ACC AGT CCC AAA GAG AAA CTT CCA GAA GGA GCT CTC CGT TTT   114
CAG TTT GCC AGT TGG CTT CCT GTC CTT CTG CGA GGA GTA CCA GTG TGA AGC ATG CAG CAG   174
                                                                Met Gln Gln
                                                                 1
```

```
GAC GGA CTC AGC AGT GTG AAT CAG CTA GGG GGA CTC TTT GTG AAT GGC CGG CCC CTT CCT    234
Asp Gly Leu Ser Ser Val Asn Gln Leu Gly Gly Leu Phe Val Asn Gly Arg Pro Leu Pro
         5                  10                  15                  20

CTG GAC ACC AGG CAG CAG ATT GTG CAG CTA GCA ATA AGA GGG ATG CGA CCC TGT GAC ATT    294
Leu Asp Thr Arg Gln Gln Ile Val Gln Leu Ala Ile Arg Gly Met Arg Pro Cys Asp Ile
         25                 30                  35                  40

TCA CGG AGC CTT AAG GTA TCT AAT GGC TGT GTG AGC AAG ATC CTA GGA CGC TAC TAC CGC    354
Ser Arg Ser Leu Lys Val Ser Asn Gly Cys Val Ser Lys Ile Leu Gly Arg Tyr Tyr Arg
         45                 50                  55                  60

ACA GGT GTC TTG GAA CCC AAG TGT ATT GGG GGA AGC AAA CCA CGT CTG GCC ACA CCT GCT    414
Thr Gly Val Leu Glu Pro Lys Cys Ile Gly Gly Ser Lys Pro Arg Leu Ala Thr Pro Ala
         65                 70                  75                  80

GTG GTG GCT CGA ATT GCC CAG CTA AAG GAT GAG TAC CCT GCT CTT TTT GCC TGG GAG ATC    474
Val Val Ala Arg Ile Ala Gln Leu Lys Asp Glu Tyr Pro Ala Leu Phe Ala Trp Glu Ile
         85                 90                  95                 100

CAA CAC CAG CTT TGC ACT GAA GGG CTT TGT ACC CAG GAC AAG GCT CCC AGT GTG TCC TCT    534
Gln His Gln Leu Cys Thr Glu Gly Leu Cys Thr Gln Asp Lys Ala Pro Ser Val Ser Ser
        105                110                 115                 120
```

FIG. 12B

```
ATC AAT CGA GTA CTT CGG GCA CTT CAG GAA GAC CAG AGC TTG CAC TGG ACT CAA CTC AGA    594
Ile Asn Arg Val Leu Arg Ala Leu Gln Glu Asp Gln Ser Leu His Trp Thr Gln Leu Arg
125                 130                 135                 140

TCA CCA GCT GTG TTG GCT CCA GTT CTT CCC CAC AGT AAC TGT GGG GCT CCC CGA            654
Ser Pro Ala Val Leu Ala Pro Val Leu Pro His Ser Asn Cys Gly Ala Pro Arg
        145                 150                 155                 160

GGC CCC CAC CCA GGA ACC AGC CAC AGG AAT CGG GCT ATC TTC TCC CCG GGA CAA GCC GAG    714
Gly Pro His Pro Gly Thr Ser His Arg Asn Arg Ala Ile Phe Ser Pro Gly Gln Ala Glu
165                 170                 175                 180

GCA CTG GAG AAA GAG TTT CAG CGT GGG CAG TAT CCA GAT TCA GTG GCC CGT GGG AAG CTG    774
Ala Leu Glu Lys Glu Phe Gln Arg Gly Gln Tyr Pro Asp Ser Val Ala Arg Gly Lys Leu
        185                 190                 195                 200

GCT GCT GCC ACC TCT CTG CCT GAA GAC ACG GTG AGG GTT TGG TTT TCT AAC AGA AGA GCC    834
Ala Ala Ala Thr Ser Leu Pro Glu Asp Thr Val Arg Val Trp Phe Ser Asn Arg Arg Ala
205                 210                 215                 220

AAA TGG CGC AGG CAA GAG AAG CTG AAA TGG GAA GCA CAG CTG CCA GGT GCT TCC CAG GAC    894
Lys Trp Arg Arg Gln Glu Lys Leu Lys Trp Glu Ala Gln Leu Pro Gly Ala Ser Gln Asp
        225                 230                 235                 240
```

FIG. 12C

```
CTG ACG ATA CCA AAA AAT TCT CCA GGG ATC ATC TCT GCA CAG CAG TCC CCC GGC AGT GTA    954
Leu Thr Ile Pro Lys Asn Ser Pro Gly Ile Ile Ser Ala Gln Gln Ser Pro Gly Ser Val
245                     250                     255                     260

CCC TCA GCT GCC TTG CCT GTG CTG GAA CCA TTG AGT CCT TCC TTC TGT CAG CTA TGC TGT   1014
Pro Ser Ala Ala Leu Pro Val Leu Glu Pro Leu Ser Pro Ser Phe Cys Gln Leu Cys Cys
        265                     270                     275                     280

GGG ACA GCA CCA GGC AGA TGT TCC AGT GAC ACC TCA TCC CAG GCC TAT CTC CAA CCC TAC   1074
Gly Thr Ala Pro Gly Arg Cys Ser Ser Asp Thr Ser Ser Gln Ala Tyr Leu Gln Pro Tyr
        285                     290                     295                     300

TGG GAC TGC CAA TCC CTC CTT CCT GTG GCT TCC TCC TCA TAT GTG GAA TTT GCC TGC CCT   1134
Trp Asp Cys Gln Ser Leu Leu Pro Val Ala Ser Ser Ser Tyr Val Glu Phe Ala Cys Pro
305                     310                     315                     320

GCC TCA CCA CCC ATC CTG TGC ATC ATC TGA TTG GAG GCC CAG GAC AAG TGC CAT CAT CCC   1194
Ala Ser Pro Pro Ile Leu Cys Ile Ile
        325                     330

ATT GCT CAA ACT GGC CAT AAG ACA CCT CTA TTT GAC AGT AAT AAA AAC CTT TTC TTA GAT   1254

GTT AAA AAA AAA GGG GGG   1275
```

FIG. 12D

FIG. 13A (2) INFORMATION FOR SEQ ID NO: 4:

(i) SEQUENCE CHARACTERESTICS:

(A) LENGTH: 332 amino acids
    (B) TYPE: amino acid
    (D) TOPOLOGY: linear (ii) MOLECULE TYPE: protein (xi) SEQUENCE DESCRIPTION : SEQ ID NO: 4:

```
                                            Met Gln Gln
                                              1
Asp Gly Leu Ser Ser Val Asn Gln Leu Gly Gly Leu Phe Val Asn Gly Arg Pro Leu Pro
          5                  10                  15                  20
Leu Asp Thr Arg Gln Gln Ile Val Gln Leu Ala Ile Arg Gly Met Arg Pro Cys Asp Ile
         25                  30                  35                  40
Ser Arg Ser Leu Lys Val Ser Asn Gly Cys Val Ser Lys Ile Leu Gly Arg Tyr Tyr Arg
         45                  50                  55                  60
Thr Gly Val Leu Glu Pro Lys Cys Ile Gly Gly Ser Lys Pro Arg Leu Ala Thr Pro Ala
         65                  70                  75                  80
```

Val Val Ala Arg Ile Ala Gln Leu Lys Asp Glu Tyr Pro Ala Leu Phe Ala Trp Glu Ile
85              90                  95                 100

Gln His Gln Leu Cys Thr Glu Gly Leu Cys Thr Gln Asp Lys Ala Pro Ser Val Ser Ser
105             110                 115                120

Ile Asn Arg Val Leu Arg Ala Leu Gln Glu Asp Gln Ser Leu His Trp Thr Gln Leu Arg
125             130                 135                140

Ser Pro Ala Val Leu Ala Pro Val Leu Pro Ser Pro His Ser Asn Cys Gly Ala Pro Arg
145             150                 155                160

Gly Pro His Pro Gly Thr Ser His Arg Asn Arg Ala Ile Phe Ser Pro Gly Gln Ala Glu
165             170                 175                180

Ala Leu Glu Lys Glu Phe Gln Arg Gly Gln Tyr Pro Asp Ser Val Ala Arg Gly Lys Leu
185             190                 195                200

Ala Ala Thr Ser Leu Pro Glu Asp Thr Val Arg Val Trp Phe Ser Asn Arg Arg Ala
205             210                 215                220

Lys Trp Arg Arg Gln Glu Lys Leu Lys Trp Glu Ala Gln Leu Pro Gly Ala Ser Gln Asp
225             230                 235                240

Leu Thr Ile Pro Lys Asn Ser Pro Gly Ile Ile Ser Ala Gln Gln Ser Pro Gly Ser Val
245             250                 255                260

FIG. 13B

```
Pro Ser Ala Ala Leu Pro Val Leu Glu Pro Leu Ser Pro Ser Phe Cys Gln Leu Cys Cys
    265             270             275             280

Gly Thr Ala Pro Gly Arg Cys Ser Ser Asp Thr Ser Ser Gln Ala Tyr Leu Gln Pro Tyr
    285             290             295             300

Trp Asp Cys Gln Ser Leu Leu Pro Val Ala Ser Ser Tyr Val Glu Phe Ala Cys Pro
    305             310             315             320

Ala Ser Pro Pro Ile Leu Cys Ile Ile
    325             330
```

FIG. 13C

FIG. 14A (2) INFORMATION FOR SEQ ID NO: 1:

(i) SEQUENCE CHARACTERISTICS:

(A) LENGTH: 2481 base pairs (B) TYPE: nucleic acid (C) STRANDEDNESS: single (D) TOPOLOGY: linear (ii) MOLECULE TYPE: other nucleic acid (A) DESCRIPTION:   /desc = "oligonucleotide"

(ix) FEATURE:

(A) NAME/KEY: CDS (B) LOCATION:163..1470

(xi) SEQUENCE DESCRIPTION: SEQ ID NO: 1:

ACAACGACGA AAGAGAGGAT GCCTCTTAAA GGCAGAAGAC TTTAACCAAG GGCGGTGAGC   60

FIG. 14B

```
AGATGTGTGA GATCTTCTAT TCTAGAAGTG GACGTATATC CCAGTTCTCA GAGCCCCGTA    120

TTCGAGCCCC GTGGGATCCG GAGGCTGCCA ACCAGCTCCA GC ATG CAG AAC AGT      174
                                              Met Gln Asn Ser
                                               1

CAC AGC GGA GTG AAT CAG CTT GGT GGT GTC TTT GTC AAC GGG CGG CCA     222
His Ser Gly Val Asn Gln Leu Gly Gly Val Phe Val Asn Gly Arg Pro
 5                   10                  15                  20

CTG CCG GAC TCC ACC CGG CAG AAG ATC GTA GAG CTA GCT CAC AGC GGG     270
Leu Pro Asp Ser Thr Arg Gln Lys Ile Val Glu Leu Ala His Ser Gly
                 25                  30                  35
```

FIG. 14C

GCC CGG CCG TGC GAC ATT TCC CGA ATT CTG CAG ACC CAT GCA GAT GCA    318
Ala Arg Pro Cys Asp Ile Ser Arg Ile Leu Gln Thr His Ala Asp Ala
             40                  45                  50

AAA GTC CAG GTG CTG GAC AAT GAA AAC GTA TCC AAC GGT TGT GTG AGT    366
Lys Val Gln Val Leu Asp Asn Glu Asn Val Ser Asn Gly Cys Val Ser
         55                  60                  65

AAA ATT CTG GGC AGG TAT TAC GAG ACT GGC TCC ATC AGA CCC AGG GCA    414
Lys Ile Leu Gly Arg Tyr Tyr Glu Thr Gly Ser Ile Arg Pro Arg Ala
     70                  75                  80

ATC GGA GGG AGT AAG CCA AGA GTG GCG ACT CCA GAA GTT GTA AGC AAA    462

FIG. 14D

```
Ile Gly Gly Ser Lys Pro Arg Val Ala Thr Pro Glu Val Val Ser Lys
 85                  90                  95                 100

ATA GCC CAG TAT AAA CGG GAG TGC CCT TCC ATC TTT GCT TGG GAA ATC    510
Ile Ala Gln Tyr Lys Arg Glu Cys Pro Ser Ile Phe Ala Trp Glu Ile
                    105                 110                 115

CGA GAC AGA TTA TTA TCC GAG GGG GTC TGT ACC AAC GAT AAC ATA CCC    558
Arg Asp Arg Leu Leu Ser Glu Gly Val Cys Thr Asn Asp Asn Ile Pro
                    120                 125                 130

AGT GTG TCA TCA ATA AAC AGA GTT CTT CGC AAC CTG GCT AGC GAA AAG    606
Ser Val Ser Ser Ile Asn Arg Val Leu Arg Asn Leu Ala Ser Glu Lys
```

FIG. 14E

```
                                                                  145
                                                                                                                  654
CAA CAG ATG GGC GCA GAC GGC ATG TAT GAT AAA CTA AGG ATG TTG AAC
Gln Gln Met Gly Ala Asp Gly Met Tyr Asp Lys Leu Arg Met Leu Asn
    135                 140                 155             160
                                                                                                                  702
GGG CAG ACC GGA AGC TGG GGC ACA CGC CCT GGT TGG TAT CCC GGG ACT
Gly Gln Thr Gly Ser Trp Gly Thr Arg Pro Gly Trp Tyr Pro Gly Thr
165                 170                 175                 180
                                                                                                                  750
TCA GTA CCA GGG CAA CCC ACG CAA GAT GGC TGC CAG CAA CAG GAA GGA
Ser Val Pro Gly Gln Pro Thr Gln Asp Gly Cys Gln Gln Gln Glu Gly
            185                 190                 195
```

FIG. 14F

```
GGG GGA GAG AAC ACC AAC TCC ATC AGT TCT AAC GGA GAA GAC TCG GAT    798
Gly Gly Glu Asn Thr Asn Ser Ile Ser Ser Asn Gly Glu Asp Ser Asp
              200                 205                 210

GAA GCT CAG ATG CGA CTT CAG CTG AAG CGG AAG CTG CAA AGA AAT AGA    846
Glu Ala Gln Met Arg Leu Gln Leu Lys Arg Lys Leu Gln Arg Asn Arg
      215                 220                 225

ACA TCT TTT ACC CAA GAG CAG ATT GAG GCT CTG GAG AAA GAG TTT GAG    894
Thr Ser Phe Thr Gln Glu Gln Ile Glu Ala Leu Glu Lys Glu Phe Glu
              230                 235                 240

AGG ACC CAT TAT CCA GAT GTG TTT GCC CGG GAA AGA CTA GCA GCC AAA    942
```

FIG. 14G

```
Arg Thr His Tyr Pro Asp Val Phe Ala Arg Glu Arg Leu Ala Ala Lys
245                 250                 255                 260

ATA GAT CTA CCT GAA GCA AGA ATA CAG GTA TGG TTT TCT AAT CGA AGG    990
Ile Asp Leu Pro Glu Ala Arg Ile Gln Val Trp Phe Ser Asn Arg Arg
                265                 270                 275

GCC AAA TGG AGA AGA AGA GAA GAG AAA CTG AGG AAC CAG AGA CAG GCC    1038
Ala Lys Trp Arg Arg Arg Glu Glu Lys Leu Arg Asn Gln Arg Gln Ala
            280                 285                 290

AGC AAC ACT CCT AGT CAC ATT CCT ATC AGC AGC TTC AGT ACC AGT        1086
Ser Asn Thr Pro Ser His Ile Pro Ile Ser Ser Phe Ser Thr Ser
```

FIG. 14H

```
                                                                              1134
GTC TAC CAG CCA ATC CCA CAG CCC ACC ACA CCT GTC TCC TTC ACA
Val Tyr Gln Pro Ile Pro Gln Pro Thr Thr Pro Val Ser Ser Phe Thr
            310             315             320

1182
TCA GGT TCC ATG TTG GGC CGA ACA GAC ACC GCC CTC ACC AAC ACG TAC
Ser Gly Ser Met Leu Gly Arg Thr Asp Thr Ala Leu Thr Asn Thr Tyr
325             330             335             340

1230
AGT GCT TTG CCA CCC ATG CCC AGC TTC ACC ATG GCA AAC AAC CTG CCT
Ser Ala Leu Pro Pro Met Pro Ser Phe Thr Met Ala Asn Asn Leu Pro
            345             350             355
```

FIG. 14I

```
ATG CAA CCC CCA GTC CCC AGT CAG ACC TCC TCA TAC TCG TGC ATG CTG    1278
Met Gln Pro Pro Val Pro Ser Gln Thr Ser Ser Tyr Ser Cys Met Leu
            360                 365                 370

CCC ACC AGC CCG TCA GTG AAT GGG CGG AGT TAT GAT ACC TAC ACC CCT    1326
Pro Thr Ser Pro Ser Val Asn Gly Arg Ser Tyr Asp Thr Tyr Thr Pro
            375                 380                 385

CCG CAC ATG CAA ACA CAC ATG AAC AGT CAG CCC ATG GGC ACC TCG GGG    1374
Pro His Met Gln Thr His Met Asn Ser Gln Pro Met Gly Thr Ser Gly
            390                 395                 400

ACC ACT TCA ACA GGA CTC ATT TCA CCT GGA GTG TCA GTT CCC GTC CAA    1422
```

FIG. 14J

```
Thr Thr Ser Thr Gly Leu Ile Ser Pro Gly Val Ser Val Pro Val Gln
405                 410                 415                 420

GTT CCC GGG AGT GAA CCT GAC ATG TCT CAG TAC TGG CCT CGA TTA CAG      1470
Val Pro Gly Ser Glu Pro Asp Met Ser Gln Tyr Trp Pro Arg Leu Gln
            425                 430                 435

TAAAGAGAGA AGGAGAGAGC ATGTGATCGA GAGAGGAAAT TGTGTTCACT CTGCCAATGA    1530

CTATGTGGAC ACAGCAGTTG GGTATTCAGG AAAGAAAGAG AAATGGCGGT TAGAAGCACT    1590

TCACTTTGTA ACTGTCCTGA ACTGGGAGCCC GGGAATGGAC TAGAACCAAG GACCTTGCGT   1650
```

FIG. 14K

```
ACAGAAGGCA CGGTATCAGT TGGAACAAAT CTTCATTTG  GTATCCAAAC TTTTATTCAT  1710
TTTGGTGTAT TATTTGTAAA TGGGCATTGG TATGTTATAA TGAAGAAAAG AACAACACAG  1770
GCTGTTGGAT CGCGGATCTG TGTTGCTCAT GTGGTTGTTT AAAGGAAACC ATGATCGACA  1830
AGATTGCCA  TGGATTTAAG AGTTTATCA  AGATATATCA AATACTTCTC CCCATCTGTT  1890
CATAGTTTAT GGACTGATGT TCCAAGTTTG TATCATTCCT TTGCATATAA TTGAACCTGG  1950
GACAACACAC ACTAGATATA TGTAAAAAACT ATCTGTTGGT TTTCCAAAGG TTGTTAACAG  2010
ATGAAGTTTA TGTGCAAAAA AGGGTAAGAT ATGAATTCAA GGAGAAGTTG ATAGCTAAAA  2070
```

FIG. 14L

```
GGTAGAGTGT GTCTTCGATA TAATACAATT TGTTTTATGT CAAAAATGTAA GTATTTGTCT    2130

TCCCTAGAAA TCCTCAGAAT GATTTCTATA ATAAAGTTAA TTTCATTTAT ATTTGACAAG    2190

AATACTCTAT AGATGTTTTA TACACATTTT CATGCAATCA TTTGTTTCTT TCTTGGCCAG    2250

CAAAAGTTAA TTGTTCTTAG ATATAGCTGT ATTACTGTTC ACAGTCCAAT CATTTTGTGC    2310

ATCTAGAATT CATTCCTAAT CAATTAAAAG TGCTTGCAAG AGTTTTAAAC CTAAGTGTTT    2370

TGCAGTTGTT CACAAATACA TATCAAAATT AACCATTGTT GATTGTAAAA AAAAAACCAT    2430

GCCAAAGCCT TTGTATTTTC TTTATTACCC TTGACCGTAA GACATGAATT C             2481
```

FIG. 15A (2) INFORMATION FOR SEQ ID NO: 2:

(i) SEQUENCE CHARACTERISTICS:

(A) LENGTH: 436 amino acids (B) TYPE: amino acid (D) TOPOLOGY: linear (ii) MOLECULE TYPE: protein (xi) SEQUENCE DESCRIPTION: SEQ ID NO: 2:

```
Met Gln Asn Ser His Ser Gly Val Asn Gln Leu Gly Gly Val Phe Val
 1               5                  10                  15
Asn Gly Arg Pro Leu Pro Asp Ser Thr Arg Gln Lys Ile Val Glu Leu
                20                  25                  30
```

FIG. 15B

Ala His Ser Gly Ala Arg Pro Cys Asp Ile Ser Arg Ile Leu Gln Thr
            35                  40                  45

His Ala Asp Ala Lys Val Gln Val Leu Asp Asn Glu Asn Val Ser Asn
        50                  55                  60

Gly Cys Val Ser Lys Ile Leu Gly Arg Tyr Tyr Glu Thr Gly Ser Ile
        65                  70                  75                  80

Arg Pro Arg Ala Ile Gly Gly Ser Lys Pro Arg Val Ala Thr Pro Glu
                85                  90                  95

FIG. 15C

Val Val Ser Lys Ile Ala Gln Tyr Lys Arg Glu Cys Pro Ser Ile Phe
              100                 105                 110

Ala Trp Glu Ile Arg Asp Arg Leu Leu Ser Glu Gly Val Cys Thr Asn
              115                 120                 125

Asp Asn Ile Pro Ser Val Ser Ser Ile Asn Arg Val Leu Arg Asn Leu
              130                 135                 140

Ala Ser Glu Lys Gln Gln Met Gly Ala Asp Gly Met Tyr Asp Lys Leu
              145                 150                 155            160

Arg Met Leu Asn Gly Gln Thr Gly Ser Trp Gly Thr Arg Pro Gly Trp

FIG. 15D

Tyr Pro Gly Thr Ser Val Pro Gly Gln Pro Thr Gln Asp Gly Cys Gln
165                 170                 175
            180                 185                 190

Gln Gln Glu Gly Gly Gly Gly Glu Asn Thr Asn Ser Ile Ser Ser Asn Gly
            195                 200                 205

Glu Asp Ser Asp Glu Ala Gln Met Arg Leu Gln Leu Lys Arg Lys Leu
210                 215                 220

Gln Arg Asn Arg Thr Ser Phe Thr Gln Glu Gln Ile Glu Ala Leu Glu
225                 230                 235                 240

FIG. 15E

Lys Glu Phe Glu Arg Thr His Tyr Pro Asp Val Phe Ala Arg Glu Arg
245                          250                         255

Leu Ala Ala Lys Ile Asp Leu Pro Glu Ala Arg Ile Gln Val Trp Phe
        260                         265                         270

Ser Asn Arg Arg Ala Lys Trp Arg Arg Glu Glu Lys Leu Arg Asn Gln
275                         280                         285

Arg Arg Gln Ala Ser Asn Thr Pro Ser His Ile Pro Ile Ser Ser Ser
        290                         295                         300

Phe Ser Thr Ser Val Tyr Gln Pro Ile Pro Gln Pro Thr Thr Pro Val

FIG. 15F

305  
Ser Ser Phe Thr Ser Gly Ser Met Leu Gly Arg Thr Asp Thr Ala Leu
310           315               320
             325                    330                335

Thr Asn Thr Tyr Ser Ala Leu Pro Pro Met Pro Ser Phe Thr Met Ala
     340                    345                350

Asn Asn Leu Pro Met Gln Pro Pro Val Pro Ser Gln Thr Ser Ser Tyr
355                    360                365

Ser Cys Met Leu Pro Thr Ser Pro Ser Val Asn Gly Arg Ser Tyr Asp
370                    375                380

FIG. 15G

Thr Tyr Thr Pro Pro His Met Gln Thr His Met Asn Ser Gln Pro Met
385             390             395             400

Gly Thr Ser Gly Thr Thr Ser Thr Gly Leu Ile Ser Pro Gly Val Ser
            405             410             415

Val Pro Val Gln Val Pro Gly Ser Glu Pro Asp Met Ser Gln Tyr Trp
            420             425             430

Pro Arg Leu Gln
        435

FIG. 16A (2) INFORMATION FOR SEQ ID NO: 3:

(i) SEQUENCE CHARACTERISTICS:

(A) LENGTH: 1275 base pairs (B) TYPE: nucleic acid (C) STRANDEDNESS: single (D) TOPOLOGY: linear (ii) MOLECULE TYPE: other nucleic acid (A) DESCRIPTION:   /desc = "oligonucleotide"

(ix) FEATURE:

(A) NAME/KEY: CDS (B) LOCATION:166..1161

(xi) SEQUENCE DESCRIPTION: SEQ ID NO: 3:

ACCAGCAACC CTGGAGCCTG CACAGACCCT GAGACCTCTT CCTGAATTCC CACCTTTTT  60

FIG.16B

```
CCTCCATCCA GTACCAGTCC CAAAGAGAAA CTTCCAGAAG GAGCTCTCCG TTTTCAGTTT    120

GCCAGTTGGC TTCCTGTCCT TCTGCGAGGA GTACCAGTGT GAAGC ATG CAG CAG        174
                                                  Met Gln Gln
                                                   1

GAC GGA CTC AGC AGT GTG AAT CAG CTA GGG GGA CTC TTT GTG AAT GGC      222
Asp Gly Leu Ser Ser Val Asn Gln Leu Gly Gly Leu Phe Val Asn Gly
         5                  10                  15

CGG CCC CTT CCT CTG GAC ACC AGG CAG CAG ATT GTG CAG CTA GCA ATA      270
Arg Pro Leu Pro Leu Asp Thr Arg Gln Gln Ile Val Gln Leu Ala Ile
 20                  25                  30                  35
```

FIG. 16C

```
AGA GGG ATG CGA CCC TGT GAC ATT TCA CGG AGC CTT AAG GTA TCT AAT    318
Arg Gly Met Arg Pro Cys Asp Ile Ser Arg Ser Leu Lys Val Ser Asn
                    40                  45                  50

GGC TGT GTG AGC AAG ATC CTA GGA CGC TAC TAC CGC ACA GGT GTC TTG    366
Gly Cys Val Ser Lys Ile Leu Gly Arg Tyr Tyr Arg Thr Gly Val Leu
            55                  60                  65

GAA CCC AAG TGT ATT GGG GGA AGC AAA CCA CGT CTG GCC ACA CCT GCT    414
Glu Pro Lys Cys Ile Gly Gly Ser Lys Pro Arg Leu Ala Thr Pro Ala
    70                  75                  80

GTG GTG GCT CGA ATT GCC CAG CTA AAG GAT GAG TAC CCT GCT CTT TTT    462
Val Val Ala Arg Ile Ala Gln Leu Lys Asp Glu Tyr Pro Ala Leu Phe
```

FIG. 16D

```
Val Val Ala Arg Ile Ala Gln Leu Lys Asp Glu Tyr Pro Ala Leu Phe
 85                      90                      95

GCC TGG GAG ATC CAA CAC CAG CTT TGC ACT GAA GGG CTT TGT ACC CAG   510
Ala Trp Glu Ile Gln His Gln Leu Cys Thr Glu Gly Leu Cys Thr Gln
100                     105                     110             115

GAC AAG GCT CCC AGT GTG TCC TCT ATC AAT CGA GTA CTT CGG GCA CTT   558
Asp Lys Ala Pro Ser Val Ser Ser Ile Asn Arg Val Leu Arg Ala Leu
                120                     125                     130

CAG GAA GAC CAG AGC TTG CAC TGG ACT CAA CTC AGA TCA CCA GCT GTG   606
Gln Glu Asp Gln Ser Leu His Trp Thr Gln Leu Arg Ser Pro Ala Val
```

FIG. 16E

```
                                                                                      654
TTG GCT CCA GTT CTT CCC AGT CCC CAC AGT AAC TGT GGG GCT CCC CGA
Leu Ala Pro Val Leu Pro Ser Pro His Ser Asn Cys Gly Ala Pro Arg
135             140             145             150             155             160

702
GGC CCC CAC CCA GGA ACC AGC CAC AGG AAT CGG GCT ATC TTC TCC CCG
Gly Pro His Pro Gly Thr Ser His Arg Asn Arg Ala Ile Phe Ser Pro
        165             170             175

750
GGA CAA GCC GAG GCA CTG GAG AAA GAG TTT CAG CGT GGG CAG TAT CCA
Gly Gln Ala Glu Ala Leu Glu Lys Glu Phe Gln Arg Gly Gln Tyr Pro
180             185             190             195
```

FIG. 16F

```
GAT TCA GTG GCC CGT GGG AAG CTG GCT GCC ACC TCT CTG CCT GAA      798
Asp Ser Val Ala Arg Gly Lys Leu Ala Ala Thr Ser Leu Pro Glu
                200                 205                 210

GAC ACG GTG AGG GTT TGG TTT TCT AAC AGA AGA GCC AAA TGG CGC AGG  846
Asp Thr Val Arg Val Trp Phe Ser Asn Arg Arg Ala Lys Trp Arg Arg
            215                 220                 225

CAA GAG AAG CTG AAA TGG GAA GCA CAG CTG CCA GGT GCT TCC CAG GAC  894
Gln Glu Lys Leu Lys Trp Glu Ala Gln Leu Pro Gly Ala Ser Gln Asp
        230                 235                 240

CTG ACG ATA CCA AAA AAT TCT CCA GGG ATC TCT ATC TCT GCA CAG TCC  942
```

FIG. 16G

```
Leu Thr Ile Pro Lys Asn Ser Pro Gly Ile Ile Ser Ala Gln Gln Ser
            245                 250                 255

CCC GGC AGT GTA CCC TCA GCT GCC TTG CCT GTG CTG GAA CCA TTG AGT    990
Pro Gly Ser Val Pro Ser Ala Ala Leu Pro Val Leu Glu Pro Leu Ser
        260                 265                 270         275

CCT TCC TTC TGT CAG CTA TGC TGT GGG ACA GCA CCA GGC AGA TGT TCC   1038
Pro Ser Phe Cys Gln Leu Cys Cys Gly Thr Ala Pro Gly Arg Cys Ser
                280                 285                 290

AGT GAC ACC TCA TCC CAG GCC TAT CTC CAA CCC TAC TGG GAC TGC CAA   1086
Ser Asp Thr Ser Ser Gln Ala Tyr Leu Gln Pro Tyr Trp Asp Cys Gln
```

FIG. 16H

```
                                                                        1134
TCC CTC CTT CCT GTG GCT TCC TCC TCA TAT GTG GAA TTT GCC TGC CCT
Ser Leu Leu Pro Val Ala Ser Ser Ser Tyr Val Glu Phe Ala Cys Pro
295             300             305             310             315             320

1181
GCC TCA CCA CCC ATC CTG TGC ATC ATC TGATTGGAGG CCCAGGACAA
Ala Ser Pro Pro Ile Leu Cys Ile Ile
                325             330

1241
GTGCCATCAT CCCATTGCTC AAACTGGCCA TAAGACACCT CTATTTGACA GTAATAAAAA

1275
CCTTTCTTA GATGTTAAAA AAAAAAAAGG GGGG
```

FIG. 17A (2) INFORMATION FOR SEQ ID NO: 4:

(i) SEQUENCE CHARACTERISTICS:

(A) LENGTH: 332 amino acids (B) TYPE: amino acid (D) TOPOLOGY: linear (ii) MOLECULE TYPE: protein (xi) SEQUENCE DESCRIPTION: SEQ ID NO: 4:

```
Met Gln Gln Asp Gly Leu Ser Ser Val Asn Gln Leu Gly Gly Leu Phe
 1               5                  10                  15
Val Asn Gly Arg Pro Leu Pro Leu Asp Thr Arg Gln Gln Ile Val Gln
                20                  25                  30
```

FIG.17B

Leu Ala Ile Arg Gly Met Arg Pro Cys Asp Ile Ser Arg Ser Leu Lys
                35                  40                  45

Val Ser Asn Gly Cys Val Ser Lys Ile Leu Gly Arg Tyr Tyr Arg Thr
            50                  55                  60

Gly Val Leu Glu Pro Lys Cys Ile Gly Gly Ser Lys Pro Arg Leu Ala
65                  70                  75                  80

Thr Pro Ala Val Val Ala Arg Ile Ala Gln Leu Lys Asp Glu Tyr Pro
                85                  90                  95

Ala Leu Phe Ala Trp Glu Ile Gln His Gln Leu Cys Thr Glu Gly Leu

FIG. 17C

```
         100                    105                      110
Cys Thr Gln Asp Lys Ala Pro Ser Val Ser Ser Ile Asn Arg Val Leu
             115                    120                    125

Arg Ala Leu Gln Glu Asp Gln Ser Leu His Trp Thr Gln Leu Arg Ser
             130                    135                    140

Pro Ala Val Leu Ala Pro Val Leu Pro Ser Pro His Ser Asn Cys Gly
             145                    150                    155                    160

Ala Pro Arg Gly Pro His Pro Gly Thr Ser His Arg Asn Arg Ala Ile
             165                    170                    175
```

FIG. 17D

Phe Ser Pro Gly Gln Ala Glu Ala Leu Glu Lys Glu Phe Gln Arg Gly
                180                 185                 190

Gln Tyr Pro Asp Ser Val Ala Arg Gly Lys Leu Ala Ala Ala Thr Ser
            195                 200                 205

Leu Pro Glu Asp Thr Val Arg Val Trp Phe Ser Asn Arg Arg Ala Lys
        210                 215                 220

Trp Arg Arg Gln Glu Lys Leu Lys Trp Glu Ala Gln Leu Pro Gly Ala
    225                 230                 235                 240

Ser Gln Asp Leu Thr Ile Pro Lys Asn Ser Pro Gly Ile Ile Ser Ala

FIG. 17E

```
    245             250             255
Gln Gln Ser Pro Gly Ser Val Pro Ser Ala Ala Leu Pro Val Leu Glu
                260             265             270

Pro Leu Ser Pro Ser Phe Cys Gln Leu Cys Cys Gly Thr Ala Pro Gly
            275             280             285

Arg Cys Ser Ser Asp Thr Ser Ser Gln Ala Tyr Leu Gln Pro Tyr Trp
        290             295             300

Asp Gln Ser Leu Leu Pro Val Ala Ser Ser Ser Tyr Val Glu Phe
305             310             315             320

Ala Cys Pro Ala Ser Pro Pro Ile Leu Cys Ile Ile
            325             330
```

PAX6 AND PAX4 NUCLEIC ACID MIXTURES

RELATED APPLICATIONS

Reference is made to the concurrently filed application of Beatriz SOSA-PINEDA and Peter GRUSS, Ser. No. 08/778,423 and to the U.S. application of Peter GRUSS and Catharina MAULBECKER, Ser. No. 08/381,841, filed Mar. 27, 1995 as the National Phase of PCT/EP93/02051, filed Aug. 2, 1993, designating the U.S. and claiming priority from German application P 42 25 569.4, filed Aug. 3, 1992. Each of the aforementioned U.S., PCT, and German applications are hereby incorporated herein by reference.

FIELD OF THE INVENTION

The present invention relates to methods for testing the differentiation status of pancreatic cells in a mammal; for instance, by ascertaining the level or status of Pax6 mRNA and/or protein in pancreatic cells (or pre-pancreatic cells) and comparing the level or status with the corresponding level or status in normal pancreatic (or pre-pancreatic) cells. This method provides a means for diagnosis or detection of diseases which arise from certain pancreatic or brain cells, especially a means for diagnosis or detection of, for instance, hypoglycemia or mental diseases. The method can be performed in conjunction with ascertaining the level or status of Pax4 mRNA and/or protein in pancreatic cells (or pre-pancreatic cells) and comparing the level or status with the corresponding level or status in normal pancreatic (or pre-pancreatic) cells.

The data set forth below shows that deficiency in Pax6 expression is indicative of deficiency or failure in α-cell development, and ergo glucagon production (and thus hypoglycemia and mental disease). The invention thus relates to restoring Pax6 expression for treatment, prevention or delaying a pancreatic or brain disease such as hypoglycemia or mental disorder from improper expression of the glucagon gene; and ergo transgenic mammals having restored Pax6 expression by modification so as to comprise at least one first nucleic acid molecule having a sequence encoding a functional and expressible Pax6 protein and optionally a second nucleic acid sequence encoding a functional and expressible Pax4 protein. Alternatively or additionally, the invention relates to administration of Pax6 alone or with Pax4 and/or of an agent for stimulating expression of Pax6 or Pax4 and Pax6, for treatment, prevention or delaying a pancreatic or brain disease such as hypoglycemia or mental disorder from improper expression of the glucagon gene.

Since the data set forth below shows that deficiency in Pax6 expression is indicative of deficiency or failure in α-cell development and ergo glucagon production (and thus hypoglycemia), the present invention also relates to transgenic mammals modified so as to comprise at least one inactivated Pax6 allele. This mammal has numerous utilities, including as a research model for pancreatic and/or brain diseases such as hypoglycemia and/or mental disorder; and therefore, presents a novel and valuable animal in the development of therapies, treatment, etc. for diseases caused by deficiency or failure of pancreatic cells. Accordingly, in this instance, the mammal is preferably non-human, e.g., a laboratory animal such as a mouse or rat.

Further, since improper expression of Pax6 may also cause maladies such as tumors, the invention also relates to a transgenic mammal modified so as to comprise at least one inactivated Pax6 allele for treatment, prevention or the delay of a pancreatic disease caused by improper expression of Pax6, such as tumors. In this instance, the mammal can be a human, as the introduction into the mammal of the at least one inactivated Pax6 allele is for therapy. The therapy also can include (in addition to the introduction of the at least one inactivated Pax6 allele) introduction into the mammal of at least one inactivated Pax4 allele. Alternatively or additionally, the invention relates to administration of an agent which inhibits Pax6 or Pax4 and Pax6 for treatment, prevention or delaying a pancreatic disease caused by improper expression of Pax6, such as tumors.

Moreover, from the data herein and in the above-referenced concurrently filed application, Pax4 and Pax6 determine the cell fate of the endocrine progenitor during development. In particular, in a first step, the Pdx1 gene defines the region of the endoderm that will give rise to pancreatic exocrine and endocrine progenitors since its expression occurs before expression of Pax genes and mice lacking Pdx1 do not form a pancreas. The onset of Pax expression in the pancreas divides endocrine progenitors into two populations: cells expressing both Pax4 and Pax6 differentiate into mature β-cells while cells expressing only Pax6 differentiate into α-cells. Absence of Pax4 diverts all progenitors into the α-cell lineage since Pax6 remains present in these cells. Deletion of Pax6 eliminates the α-cells lineage altogether or may divert progenitors to the β-cells lineage. When both Pax4 and Pax6 are absent, progenitors fail to develop into mature endocrine cells. Thus both Pax genes are required for endocrine cell differentiation during pancreatic development.

Accordingly, the present invention further relates to methods for testing the differentiation status of pancreatic cells in a mammal by ascertaining the level or status of Pax4 and Pax6 mRNA and/or protein in pancreatic cells (or pre-pancreatic cells) and comparing the level or status with the corresponding level or status in normal pancreatic (or pre-pancreatic) cells. This method provides a means for diagnosis or detection of diseases which arise from certain pancreatic cells, especially a means for diagnosis or detection of, for instance, diabetes, such as juvenile diabetes, and/or hypoglycemia.

Additionally the invention relates to restoring Pax4 and Pax6 expression for treatment, prevention or delaying a pancreatic disease such as diabetes, e.g., juvenile diabetes and/or hypoglycemia; and ergo transgenic mammals having restored Pax4 and Pax6 expression by modification so as to comprise at least one first nucleic acid molecule having a sequence encoding a functional and expressible Pax4 protein and a second nucleic acid sequence encoding a functional and expressible Pax6 protein. Alternatively or additionally, the invention relates to administration of Pax4 with Pax6 and/or of an agent for stimulating expression of Pax4 and Pax6, for treatment, prevention or delaying a pancreatic disease such as diabetes, e.g., juvenile diabetes and/or hypoglycemia.

Several documents are cited throughout the text of this specification. Each of the documents cited herein (including manufacturer's specifications, instructions, etc.) are hereby incorporated herein by reference.

BACKGROUND OF THE INVENTION

The pancreas is an essential organ possessing both an exocrine function involved in the delivery of enzymes into the digestive tract and an endocrine function by which various hormones are secreted into the blood stream. The exocrine function is assured by acinar and centroacinar cells that produce various digestive enzymes (amylase, proteases, nuclease, etc.) and intercalated duct cells that transport these enzymes in alkaline solution to the duodenum.

The functional unit of the endocrine pancreas is the islet of Langerhans which are scattered throughout the exocrine portion of the pancreas and are composed of four cell types: α-, β-, δ- and PP-cells, reviewed in Slack, Development 121 (1995), 1569–1580. β-cells produce insulin, represent the majority of the endocrine cells and form the core of the islets, while α-cells secrete glucagon and are located in the periphery. δ-cells and PP-cells are less numerous and respectively secrete somatostatin and a pancreatic polypeptide. Insulin and glucagon are key regulators of blood glucose levels. Insulin lowers blood glucose level by increasing the cellular uptake of glucose and its conversion to glycogen. Glucagon elevates blood glucose levels by intervening with the breakdown of liver glycogen. Common pancreatic disorders affecting endocrine function include Diabetes mellitus and hormone secreting tumors.

All four endocrine cells are thought to originate from a common pluripotent precursor that is derived from the endoderm. Early during pancreatic development, these precursors co-express several hormones such as insulin and glucagon. In mouse, the α-cells are the first endocrine cells to differentiate at day 9.5 post-conception (p.c.), followed by the β- and δ-cells at day 14.5 p.c. and the PP-cells at postnatal day 1. Very little is known on the molecular and genetic factors involved in defining the lineage of the different endocrine cells. One of the few genes described so far is the homeobox gene Pdx1 which is expressed during the initial stages of pancreatic development and becomes restricted to the β-cells in adult islets (Guz et al., Development 121 (1995), 11–18). Homozygous mouse Pdx1 mutants fail to develop a pancreas and die a few days after birth (Jonsson et al., Nature 371 (1994), 606–609). Two members of the Pax gene family, Pax6 and Pax4, are also expressed in endocrine cells during pancreatic development. Until now, however, it was not known how in particular the Pax6 and the Pax4 gene affects pancreatic development.

A method for testing for a variety of differentiation parameters in the pancreas was hitherto not available but is nevertheless highly desirable. Results obtainable by such a method would be expected to have a significant impact on, e.g., the diagnosis and therapy of pancreas related diseases.

SUMMARY OF THE INVENTION

The present invention relates to a novel method for testing the differentiation status of pancreatic cells in mammals. The present invention further relates to applications in the medical field that directly arise from the method of the invention. Additionally, the present invention relates to transgenic mammals comprising at least one inactivated Pax6 gene and optionally at least one inactivated Pax4 gene.

DETAILED DESCRIPTION OF THE INVENTION

Accordingly, a technical problem underlying the present invention was to provide such a method for monitoring the differentiation status of pancreatic cells. The solution to said technical problem is achieved by the embodiments characterized in the claims.

Thus, the present invention relates to a method for testing the differentiation status in pancreatic cells of a mammal comprising (a) determining the level or status of Pax6 mRNA in pancreatic cells of said mammal; and/or (b) determining the level or status of Pax6 protein in pancreatic cells of said mammal; and (c) comparing said level or status of Pax6 mRNA and/or Pax6 protein with the corresponding level in normal pancreatic cells.

In connection with the present invention, the term "level" denotes the amount of mRNA or protein produced. The term "status" includes the options that the gene, mRNA, protein or a transcription control element, e.g. promoter/enhancer sequence may bear a mutation, deletion or any other modifications which would affect the overall activity of the gene when compared to the wild-type normal gene product. Included in this term are post-translational modifications of the protein.

In accordance with the present invention, it was surprisingly found that Pax6 is expressed in the pancreas.

The method of the present invention allows for the first time a detailed study of the development of different cell types, i.e. α-, β-, δ- and PP-cells in the pancreatic tissue. As is demonstrated by the appended examples, the Pax6 gene, optionally in conjunction with the Pax4 gene is involved in the early steps of pancreatic development. This surprising result allows the monitoring of cell fate as well as the investigation of the development of diseases which arise from certain cell types contained in the pancreas. The results presented in accordance with the present invention furthermore allow the conclusion that Pax6 and/or Pax4 are master regulators for specific pancreatic cells. Thus, Pax6 appears to be a master regulator of α-cells. Pax6 is also expressed in non-pancreatic cells. Pax6 expression is detected in a subset of cells found in the developing spinal cord. In particular, expression of the Pax6 gene is observed in the prospective forebrain and hindbrain and is maintained in the brain, eye and neural tube throughout development (Grindley et al., Development 121 (1995), 1433–1442; Stoykova et al., Development 122 (1996), 3453–3465). Therefore, Pax6 may likewise play a role in the differentiation status of these cells. The lack of Pax6 gene expression can be monitored by using the marker "Small eyes".

Accordingly, the method of the present invention provides a means for diagnosis or detection of diseases which arise from certain cells such as pancreas cells and brain cells, especially a means for early diagnosis or detection; for instance, detection or diagnosis of hypoglycemia or mental diseases.

In a preferred embodiment, the method of the present invention further comprises (d) determining the level or status of Pax4 mRNA in pancreatic cells of said mammal; and/or (e) determining the level or status of Pax4 protein in pancreatic cells of said mammal; and (f) comparing said level or status of Pax4 mRNA and/or Pax4 protein with the corresponding level in normal pancreatic cells.

This embodiment of the present invention allows the study of the synergistic effects of the Pax6 and the Pax4 gene products. It is expected that the analysis of said synergistic effect provides deeper insights into the regulation of cell specific development in the pancreas. From said deeper insight the development of diagnostic and pharmaceutical compositions related to pancreas-specific diseases will greatly benefit.

In a further preferred embodiment of the method of the invention, said mammal is in the (i) embryonic;

(ii) newborn; or (iii) adult stage.

As has been shown in accordance with the present invention, the Pax6 gene, preferably in conjunction with the Pax4 gene, is expressed at a different level and at different stages of mammalian pancreas and brain development. The specific analysis of the developmental stage of pancreatic cells at the embryonic, newborn or adult stage will provide further insights into, e.g., specific disease states associated with the respective stages. For example, it is expected that the etiology of, e.g., hypoglycemia will be elucidated by applying the method of the present invention, as well as by employing the transgenic mammals (non-human) according to the invention (discussed infra; see also the examples). Additionally, it is expected that with the knowledge obtained from studying the expression of Pax6 in the pancreas and by employing the transgenic mammals (non-human) according to the invention (discussed infra; see also the examples), insights into the etiology and treatment of mental diseases will be attained. This is because it is known that the Pax6 gene product and the glucagon gene are expressed in the brain (Drucker and Asa, J. Biol. Chem. 263 (1988), 13475–13478; Lee et al., Endocrinology 127 (1990), 2217–2222; Lui et al., Endocrinology 126 (1990) 110–117; Han et al., J. Neurosci. Res. 16 (1986), 97–107). Upon the basis of this knowledge, new pharmaceutical active drugs, e.g. against hypoglycemia and mental diseases, will be developed and tested.

The method of the invention can be applied to a variety of mammals, depending on the purpose of the investigation. Thus, in a preferred embodiment, the mammal is a mouse. This embodiment is particularly useful for basic research to understand more clearly the functional interrelationship of different proteins which regulate the development of the pancreas. In a further embodiment the mammal is a human. In this embodiment, preferably diagnostic and therapeutic applications are envisaged.

In a further preferred embodiment of the method of the invention, steps (a) and optionally (d) and/or (b) and optionally (e) are carried out in vivo.

This embodiment of the invention is expected to be useful in particular in basic research or in therapeutic applications.

In a further preferred embodiment of the method of the invention, steps (a) and optionally (d) and/or (b) and optionally (e) are carried out in vitro.

The advantages of this embodiment would be expected to lie primarily in diagnostic applications and, again, in basic research.

In a further preferred embodiment of the method of the invention, said determination in step (a) and optionally in step (d) is effected by employing (i) a nucleic acid sequence corresponding to at least a part of the Pax6 gene and preferably encoding at least part of the Pax6 protein and optionally a second nucleic acid sequence corresponding to at least a part of the Pax4 gene and preferably encoding at least part of the Pax4 protein;

(ii) a nucleic acid sequence complementary to the nucleic acid sequence(s) of (i); or (iii) a primer or a primer pair hybridizing to the nucleic acid sequence(s) of (i) or (ii).

In accordance with this embodiment of the present invention, the method of testing the differentiation status can be effected by using a nucleic acid molecule encoding the Pax6 gene and/or the Pax4 gene or a part thereof, e.g., in the form of a Southern or Northern blot or in situ analysis. Said nucleic acid sequence may hybridize to a coding region of either of the genes or to a non-coding region. In the case that a complementary sequence in accordance with (ii) is employed in the method of the invention, said nucleic acid molecule can again be used in Northern blots. Additionally, said testing can be done in conjunction with an actual blocking, e.g., of the transcription of the gene and thus may have therapeutic relevance. Furthermore, a primer or oligonucleotide can also be used for hybridizing to one of the above-mentioned Pax genes or corresponding mRNAs. The nucleic acids used for hybridization can, of course, be conveniently labeled by incorporating or attaching, e.g., a radioactive or other marker. Such markers are well known in the art. The labeling of said nucleic acid molecules can be effected by conventional methods.

Additionally, the presence or expression of Pax6 and optionally Pax4 can be monitored by using a primer pair that specifically hybridizes to either of the corresponding nucleic acid sequences and by carrying out a PCR reaction according to standard procedures.

Specific hybridization of the above mentioned probes or primers preferably occurs at stringent hybridization conditions. The term "stringent hybridization conditions" is well known in the art; see, for example, Sambrook et al., "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985.

Further modifications of the above-mentioned embodiment of the invention can be easily devised by the person skilled in the art.

An additional embodiment of the present invention relates to a method wherein said determination in step (b) and optionally of step (e) is effected by employing an antibody or fragment thereof that specifically binds to the Pax6 protein and optionally by employing a second antibody or fragment thereof which specifically binds to the Pax4 protein.

Antibodies or fragments thereof to the aforementioned protein can be obtained by using conventional methods which are described, e.g., in Harlow and Lane "Antibodies, A Laboratory Manual", CSH Press, Cold Spring Harbor, 1988. These antibodies may be monoclonal antibodies or comprised in polyclonal antisera or fragments thereof. The antibody used in the method of the invention may be labeled with detectable tags such as a histidine flags or a biotin molecule.

In a further preferred embodiment of the method of the present invention, said pancreatic cells are α-cells or β-cells.

In accordance with the present invention, it was found that Pax6 is expressed in α-cells and β-cells. Disruption of the Pax6 gene function therefore allows a close monitoring of the development of said cells in the pancreas. Since Pax4 is also expressed in β-cells (see concurrently filed application Ser. No. 08/778,423 incorporated herein by reference), Pax6 expression may be required to establish a competent background for Pax4 to act.

Since both Pax6 and Pax4 are regulatory proteins required for proper differentiation of endocrine cells, this embodiment may allow a variety of conclusions with regard to the generation of diseases such as pancreatic tumors.

Accordingly, a further preferred embodiment relates to a method wherein said differentiation status is indicative of a malignancy or malignant potential of said pancreatic cell.

Overexpression or absence of a functional Pax6 and optionally Pax4 product may induce normal endocrine cells to become cancerous. In accordance with this statement, allelic deletions in chromosome 7q in the vicinity of the Pax4 gene are observed in many pancreatic carcinomas (Alberto et al., Cancer Res. 56 (1996), 3808–3818). Pax6, and optionally Pax4, may also interact with other oncogenic factors.

Malignancy or malignant potential is used in accordance with this invention preferably but not exclusively in connection with pancreatic tumors such as insulinoma, glucagonomas, somatostatinomas and ductal cell adenocarcinomas.

The present invention relates in a further preferred embodiment to a method that further comprises (a') prior to said testing removal of a solid pancreatic tumor from said mammal; and (b') after said testing, at least partial elimination of the expression of the Pax6 and optionally the Pax4 gene in cells of said tumor, if said gene(s) is/are over-expressed or stimulation of expression of the Pax6 gene and optionally the Pax4 gene or introduction of a functional and expressible Pax6 gene and optionally a functional and expressible Pax4 gene into said cells if said gene(s) is/are under-expressed or not expressed; and (b") reintroducing the cells obtained as a product of step (b') into said mammal.

In this context, and as used throughout this specification "functional" Pax6 (Pax4) means a protein having part or all of the primary structural conformation of the Pax6 (Pax4) protein possessing the biological property of contributing to the development of endocrine cells into α-cells and Langerhans cells (β-cells), said protein being the product of procaryotic or eukaryotic expression of a Pax6 (Pax4) encoding DNA sequence and having an amino acid sequence comprising the amino acid sequence of SEQ ID No. 2 (SEQ ID No. 4) or any fragment or derivative thereof by way of amino acid deletion, substitution, insertion, addition and/or replacement of the amino acid sequence given in SEQ ID No. 2 (SEQ ID No. 4). Also comprised by the term "functional" Pax6 (Pax4) protein is the capability of said protein or part thereof to generate a specific immune response such as an antibody response.

This embodiment of the present invention is suited for therapy of tumors, in particular in humans. Therefore, it is envisaged that pancreatic tumor cells are monitored for the expression level of the Pax6 protein and optionally Pax4 protein. Detection of an over-expression of said protein(s) would allow the conclusion that said over-expression is interrelated to the generation or maintenance of the tumor. Accordingly, a step would be applied to reduce the expression level to normal levels. This can be done, for example, by at least partial elimination of the expression of the Pax6 gene by biological means, for example, by the use of ribozymes, antisense nucleic acid molecules or intracellular antibodies against either the Pax6 or Pax4 protein. Furthermore, pharmaceutical products may be developed that reduce the expression levels of Pax6. While it is presently unclear how Pax6 and optionally Pax4 are regulated in pancreatic tissue, it is possible that different developmental and hormonal factors determine the levels of activity of these genes. For example, small molecules are known to repress the expression of certain genes. It has been demonstrated that activin A, a member of the TGFβ superfamily, can downregulate Pax6 expression in the developing spinal cord (Pituello et al., Proc. Natl. Acad. Sci. USA 92 (1995), 6952–6956). Similar molecules may downregulate Pax6 or optionally Pax4 expression in the pancreas. On the other hand, lack of expression or under-expression may be remedied by a functional Pax6 gene and optionally a functional Pax4 gene which should both be expressible in the tumor cells. Stimulation or induction of expression can be obtained again by the use of small molecules or other means, this time activating Pax6 gene expression. In this regard, it is important to note that the present invention envisages the possibilities that one of said Pax genes is over-expressed whereas the second Pax gene is under-expressed in said malignant state. Finally, surgical removal or chemotherapeutic treatment of pancreatic tumors in humans often leaves the patient without a significant number of glucagon producing cells. Pax6 and optionally Pax4 may be used in tissue engineering (Langer and Vacanti, Science 260 (1993), 920–924) for the development of functional substitutes for missing or damaged α- and β-cells. Pancreatic tumor cells that have reverted in vitro to a normal levels of Pax6 expression, and optionally of Pax4 expression, can be re-introduced into the patient so that the said patient is provided with normal glucagon- and optionally insulin-producing cells of his own genetic background thereby reducing the risk of immunological rejection of the cells.

In a further preferred embodiment of the present invention, the testing for differentiation status in pancreatic cells is a testing for the developmental status in α-cells, which as shown by the examples, is indicative of hypoglycemia. Hypoglycemia is often the result of deficiency or failure in α-cell development. The examples show that deficiency in Pax6 expression is indicative of deficiency or failure in α-cell development and ergo in glucagon production (and thus hypoglycemia).

Early diagnosis of hypoglycemia is particularly advantageous and of considerable medical importance. Thus, it is a preferred embodiment to employ methods of the invention for diagnosis or detection of hypoglycemia. This preferred embodiment can be used to diagnose hypoglycemia in the coronar villi, i.e. prior to the implantation of the embryo. Furthermore, hypoglycemia can, with the method of the present invention, be diagnosed via amniocentesis. The early diagnosis of hypoglycemia in accordance with all applications of the methods of the invention allows for treatment directly after birth before the onset of clinical symptoms.

In a particularly preferred embodiment of the method of the invention, said testing for differentiation status in said α-cells is carried out in an embryonic or newborn mammal.

As has been indicated hereinabove, it is particularly preferred to include at least one further step in the method of the invention, which is specific for different pharmaceutical and genetic therapeutic approaches. As mentioned above, different small pharmaceutically active molecules could be used to activate Pax6 and therefore induce differentiation and production of glucagon producing α-cells and the development of Langerhans islets. Likewise, intracellular targeting of active Pax6 would advance similar consequences. In accordance with this statement, pancreatic ductal epithelial cells have been proposed to contain potential stem cells for endocrine cells types. Induction of Pax6 activity in said cells but not exclusively in said cells are expected to promote differentiation into glucagon producing cells.

In a further preferred embodiment of the method of the invention, said differentiation status of pancreatic cells is the result of the activity of a medicament or of a gene therapy approach. For example, said differentiation status may be influenced by gene therapy approaches where an functional Pax6 and optionally Pax4 gene is introduced in vivo into cells using a retrovirus vector (Naldini et al., Science 272

(1996), 263–267; Mulligan, Science 260 (1993), 926–932) or other appropriate vectors. Likewise, in accordance with the present invention, cells from a patient can be isolated, modified in vitro to differentiate into α-cells and Langerhans islets of β-cells using standard tissue culture techniques and reintroduced into the patient.

In a particularly preferred embodiment, said medicament or gene therapy approach affects the expression level of the Pax6 gene and, optionally, of the Pax4 gene at the mRNA or protein level.

The above embodiments of the present invention allow, inter alia, testing of a medicament for its influence on expression of the aforementioned Pax genes. As has been stated further hereinabove, abnormal expression levels of Pax6 and optionally of Pax4 are expected to be a causative agent in the generation of, for example, solid tumors of the pancreas. The method of the invention thus allows the testing of medicaments, the application of which would allow the cell to return to a normal expression level. Said normal expression level would be expected to have a direct influence on, e.g., the malignancy of a cell. For example, if a disease or tumor is a direct or indirect result of an under-expression of Pax6, the physician treating the respective patient would administer a medicament that stimulates expression of Pax6.

In a further preferred embodiment of the method the invention, the testing for differentiation status in pancreatic cells is a testing for the developmental status in Pax6 knockout mice that are optionally at the same time Pax4 knockout mice.

In an additional preferred embodiment of the method of the present invention, said method further comprises introducing a functional and expressible Pax6 gene and optionally further comprising introducing a functional and expressible Pax4 gene into ductal epithelial cells which possess a similar yet different differentiation pathway as compared to α- and β-cells. With this embodiment of the invention, the person skilled in the art is in the position to redirect the fate of ductal epithelial cells into α- and β-cells. Thus, said cells are expected to differentiate after transfection with the Pax6 gene into α-cells and the β-cells to form Langerhans islets. A corresponding pharmaceutical application is envisaged, if a patient suffers from a α-cell- and thus glucagon deficiency. It is envisaged that this method is carried out in vitro or in vivo.

The present invention further relates to a transgenic mammal comprising at least one inactivated Pax6 allele. As to research uses of the transgenic mammal especially, it is preferred that the mammal be non-human.

The transgenic animal of the present invention can advantageously be used for monitoring the development of different cells, for example, in the pancreas. However, the use of the transgenic mammal is not confined to the study of pancreatic development. Since Pax6 is, in accordance with the present invention, now believed to be a master regulator for α-cells, its influence can also be studied in other cell types of the body.

Since the transgenic animal of the invention which is preferably a transgenic mouse in the homozygous state has severe pancreatic and neuronal disorders that, in the case of transgenic mice, lead to death within a few minutes after birth, said transgenic animal can further be used for the investigation of diseases associated with developmental disorders, in particular in the pancreas and the brain. Since the transgenic mice are deficient in glucagon producing cells and present clinical symptoms similar to human patients suffering from hypoglycemia, said mice can serve has an animal model for therapeutic and pharmaceutical research against hypoglycemia. For the same reasons as set out hereinabove, said transgenic mammals, preferably said transgenic mice, can be used as a model system to study mental diseases.

Preferably, the transgenic mammal of the invention further comprises at least one inactivated Pax4 allele.

This embodiment allows the study of the interaction of Pax6 and Pax4 on the development of the mammal or certain tissues thereof, in particular, of the pancreas. All the applications that have been herein before discussed with regard to the Pax6 transgenic mammal also apply to the mammal that carries two transgenes. It might be also desirable to inactivate Pax6 gene expression and optionally Pax4 gene expression at a certain stage of development and/or life of the transgenic animal. This can be achieved by using, for example, tissue specific, developmental and/or cell regulated and/or inducible promoters which drive the expression of, e.g., an antisense or ribozyme directed against the RNA transcript encoding the Pax6 protein and optionally to the Pax4 encoding RNA. A suitable inducible system is for example tetracycline-regulated gene expression as described, e.g., by Gossen and Bujard (Proc. Natl. Acad. Sci. 89 USA (1992), 5547–5551) and Gossen et al. (Trends Biotech. 12 (1994), 58–62).

Accordingly, in this embodiment, the transgenic mammal is preferably non-human, e.g., a laboratory animal such as a mouse or rat.

In another preferred embodiment of the invention said transgenic mammal is human, a mouse or a rat. Since at least one inactivated Pax6 allele can be introduced into a mammal for therapeutic applications, as discussed above, the transgenic animal can be a human.

In accordance with the present invention, the transgenic animal may be homozygous or heterozygous for either inactivated Pax4 or inactivated Pax6 or for both inactivated genes.

Moreover, the present invention relates to the use of and methods employing at least one first nucleic acid sequence encoding a functional and expressible Pax6 protein and optionally a second nucleic acid sequence encoding a functional and expressible Pax4 protein for the preparation of a pharmaceutical composition for treating, preventing and/or delaying hypoglycemia and/or neuronal disorders in a mammal. According to the invention, vectors containing said nucleic acid sequences may be operatively linked to regulatory elements allowing for expression of said nucleic acid sequences and/or for targeting of said nucleic acid sequences to pancreatic cells.

Further, the invention relates to the use of a functional Pax6 protein and optionally a functional Pax4 protein for the preparation of a pharmaceutical composition for the treatment, prevention and/or delay of hypoglycemia and/or a neuronal disorder in a mammal. The term "functional" bears the same meaning as outlined herein-above.

Preferably, the mammal referred to in the above embodiments is a human, a rat or a mouse. And thus, the invention further comprehends a transgenic mammal modified so as to comprise at least one first nucleic acid molecule comprising a sequence encoding a functional and expressible Pax6 protein and optionally a second nucleic acid molecule comprising a sequence encoding a functional and expressible Pax4 protein (wherein the mammal has expression of the nucleic acid molecule(s)). The mammal can be modified pre-natally or post-natally, e.g., after a method of the present invention shows low, impaired or no Pax6 protein or mRNA, for treatment, prevention or delaying hypoglycemia or mental disease; and, the modification can be by techniques discussed herein or by techniques within the ambit of the skilled artisan, without undue experimentation from this disclosure.

It is envisaged by the present invention that the nucleic acids and proteins are administered either alone or in any combination, and optionally together with a pharmaceutically acceptable carrier or excipient. Said nucleic acid sequences may be stably integrated into the genome of the mammal. On the other hand, viral vectors may be used which are specific for certain cells or tissues, preferably pancreas and/or brain, and which persist in said cells thereby conferring expression of the Pax genes in said cells. Suitable pharmaceutical carriers and excipients are well known in the art. Elements capable of targeting a nucleic acid molecule and/or protein to specific cells are described in the prior art, for example, Somia et al., Proc. Natl. Acad. Sci., USA 92 (1995), 7570–7574. The pharmaceutical compositions can be administered to the mammal at a suitable dose, which can be determined from this disclosure and knowledge in the art, without undue experimentation by the skilled artisan taking into consideration typical factors such as the species, age, sex, weight, condition of the mammal, the route of administration, whether a Pax6 protein or Pax4 and Pax6 proteins are being administered, whether an agent for inhibiting or stimulating Pax6 or Pax4 and Pax6 is being administered, whether a nucleic acid or acids are being administered, and whether the nucleic acid or acids are for expression of Pax6 or Pax4 and Pax6 or are for inhibiting expression of Pax6 or Pax4 and Pax6, inter alia. A typical dose can be, for example, in the range of 0.001 to 1000 ug (or of nucleic acid for expression or for inhibition of expression in this range); however, doses below or above this exemplary range are envisioned, especially considering the aforementioned factors.

Administration of the suitable compositions may be effected in different ways, e.g., by intravenous, intraperitoneal, subcutaneous, intramuscular, topical or intradermal administration. The pharmaceutical compositions prepared according to the invention can be used for the prevention or treatment or delaying of different kinds of diseases, for example, pancreas related diseases, namely hypoglycemia or different kinds of acquired or in-born neural disorders, neural degenerations and related disorders such as mental diseases. Said diseases and disorders are preferably derived from endocrine or neural tissues, e.g. pancreas and brain.

Furthermore, it is possible to use a pharmaceutical composition which comprises a nucleic acid sequence which encodes a Pax6 protein and optionally a nucleic acid sequence encoding a Pax4 protein for gene therapy. Naturally, both sequences may be also comprised in the same vector. As described above, the diseases often evolve when cells lose both functional copies of the Pax genes. In such a case, introduction of functional copies of the corresponding gene may help to ameliorate the situation. For example, research pertaining to gene transfer into cells of the germ line is one of the fastest growing fields in reproductive biology. Gene therapy, which is based on introducing therapeutic genes into cells by ex-vivo or in-vivo techniques is one of the most important applications of gene transfer. In genetic diseases the introduction of a normal or a functionally adequate allele of a mutated nuclear gene represents gene replacement therapy, which is applicable mainly to monogenetic recessive disorders such as, for example, diabetes and hypoglycemia.

Thus, in a further embodiment, the invention relates to a method for treating hypoglycemia comprising:

(a) removal of a cell from a mammal;

(b) introduction of a functional and expressible Pax6 gene and optionally a functional and expressible Pax4 gene into said cell; and (c) reintroducing the cell obtained as a product of step (b) into said mammal or into a mammal of the same species.

Yet, in a further embodiment, the invention relates to a the method for treating a neuronal disorder comprising:

(a) removal of a cell from a mammal;

(b) introduction of a functional and expressible Pax6 gene and optionally a functional and expressible Pax4 gene into said cell; and (c) reintroducing the cell obtained as a product of step (b) into said mammal or into a mammal of the same species.

It is to be understood that the introduced genes are functional and expressible after introduction into said cell and preferably remain in this status during the lifetime of said cell.

Preferably, said mammal is a human, rat or mouse.

In a preferred embodiment of the method of the invention, said cell is a germ line cell or embryonic cell or derived therefrom. In a most preferred embodiment, said cell is an egg cell or derived therefrom.

Suitable vectors and methods for in-vitro or in-vivo gene therapy are described in the literature and are known to the person skilled in the art. The pharmaceutical compositions according to the invention can be used for the treatment of kinds of diseases hitherto unknown as being related to the expression and/or non-expression of the Pax6 gene and/or the Pax4 gene.

BRIEF DESCRIPTION OF THE DRAWINGS

This disclosure may best be understood in conjunction with the accompanying drawings, incorporated herein by reference, which show:

FIG. 1 (FIGS. 1a, 1b, 1c). Targeted replacement of Pax6 by the β-galactosidase gene and generation of heterozygous mice.

Structure of wild type and targeted Pax6 loci. Deletion of the Pax6 initiation codon and the entire paired domain was produce by inserting the β-galactosidase-neomycin cassette pGNA developed by Philippe Brulet (Le Mouellic, H., et al., Proc. Natl. Acad. Sci. U.S.A. 87 (1990), 4712–4716). Abbreviations: A, ATG; B, Bam HI; K, Kpn I; RV, Eco RV; S, Spe I.

FIG. 2 (FIGS. 2a, 2b, 2c, 2d, 2e, 2f, 2g, 2h). β-galactosidase activity in heterozygous Pax6-LacZ embryos at different stages of development.

Pax6/β-galactosidase staining was first detected in the open neural plate and closed neural fold (arrowheads) of day 8.0 embryos. At day 8.5, strong β-galactosidase staining was observed in the prospective forebrain (f) and hindbrain (h) and progressed caudaly has the neural tube (n) closed. No expression was detected in the prospective midbrain (m) region. At day 9.5, the forebrain divides into the telencephalon (t), diencephalon (d) and the optic vesicle forms. Strong β-galactosidase activity was also detected in the hindbrain, neural tube and developing pancreas (arrowhead). Expression was maintained in the brain, eye, neural tube and pancreas throughout development and persisted in some cells of the adult animal.

Figure 2A:
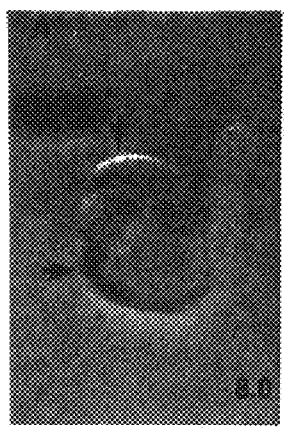
Figure 2B:
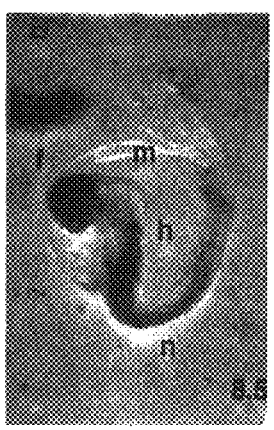
Figure 2C:
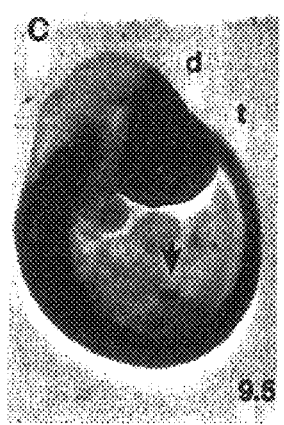
Figure 2D:
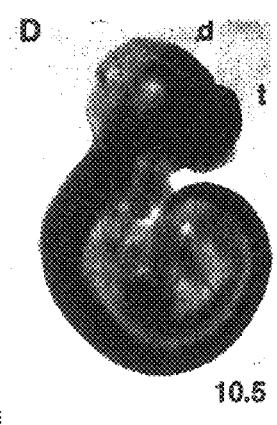
Figure 2E:
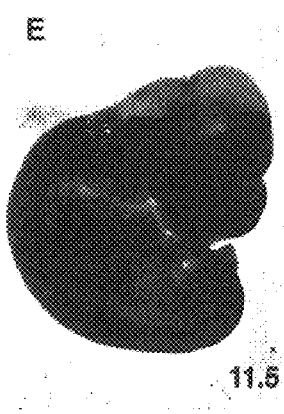
Figure 2F:
Figure 2G:
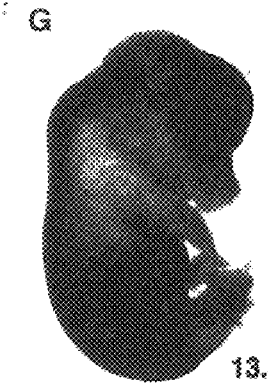
Figure 2H:
Figures 3A, 3B:
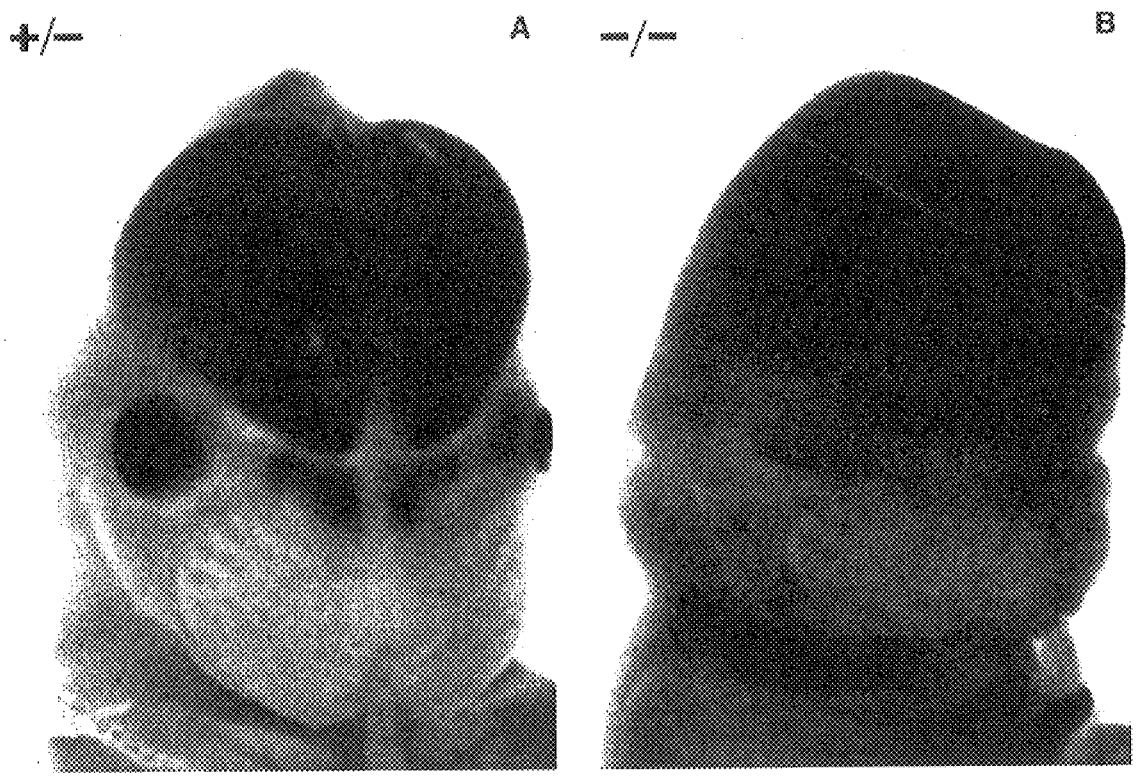

FIG. 3 (FIGS. 3a, 3b). β-galactosidase activity in homozygous Pax6-LacZ at day 13.5 p.c.

−/− animals lacked eyes and olfactory bulb (arrowhead)

Figure 4A:
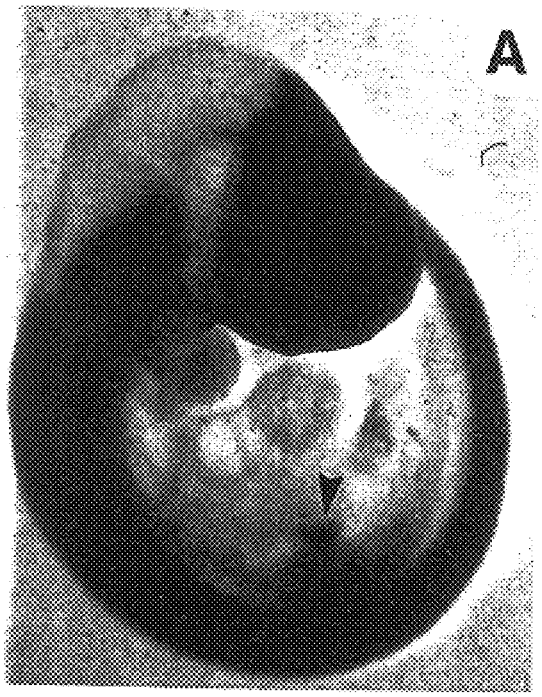
Figure 4B:
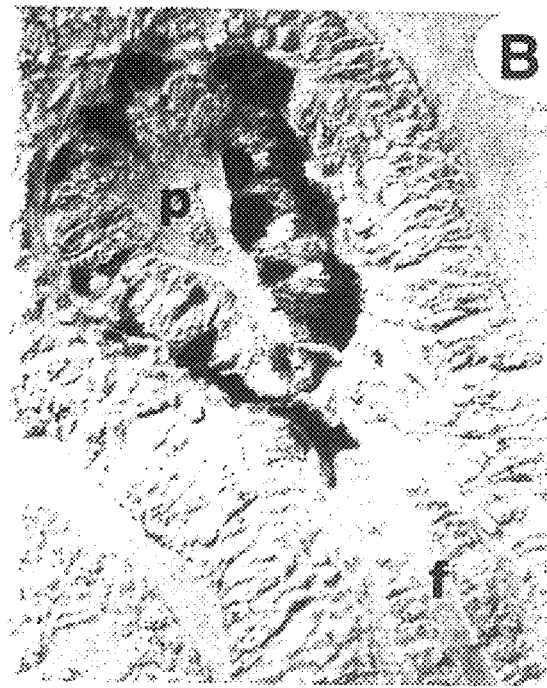
Figure 4C:
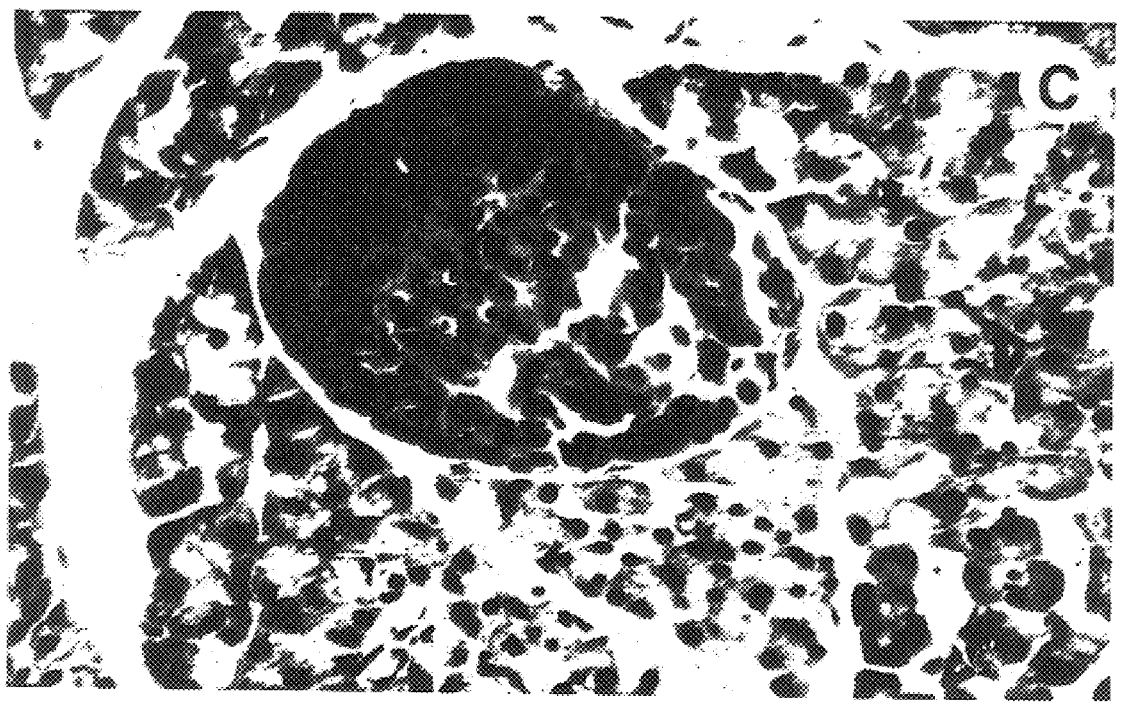

FIG. 4 (FIGS. 4a, 4b, 4c). β-galactosidase activity in embryo and newborn pancreas of heterozygous Pax6-LacZ mice.

a, β-galactosidase activity in day 9.0 p.c. +/− embryo. Strong staining is detected in the prosencephalon, diencephalon, optic vesicle, neural tube and pancreas (arrowhead).

b, Sagittal section of day 10.0 p.c. +/− embryo. Only a subset of cells in the pancreatic bud were stained blue corresponding to positive β-galactosidase expression. Magnification, ×400. Abbreviations: f, foregut; p, pancreatic bud.

c, Newborn pancreas stained for β-galactosidase activity and counterstained hematoxylin-eosin. Blue β-galactosidase positive cells were found only islets of Langerhans indicating that Pax6 is expressed endocrine cells only.

FIG. 5 (FIGS. 5a, 5b, 5c, 5d, 5e, 5f). Analysis of β-galactosidase, insulin and glucagon expression in newborn pancreases of +/− and −/− Pax6 deficient mice.

β-galactosidase staining is restricted to islet of Langerhans of +/− mice (a, b, c). Blue stained cells expressed either insulin (a) or glucagon (b, c). Insulin-producing cells form the core of the islet while glucagon-producing cells are located at the periphery (marked by arrowhead). In −/− mice (d, e, f), β-galactosidase positive cells expresses insulin only and failed to organize into islet-like structures. Panels a, b and d, e are adjacent sections. Magnification is ×200.

FIG. 6 (FIGS. 6a, 6b). Analysis of insulin and glucagon expression in newborn pancreas of homozygous Small eye mouse mutant.

Pancreas of homozygous Small eye animal produce only insulin (arrowhead). Insulin-producing cells were not organized in islets of Langerhans but remained scattered throughout the exocrine tissue. Glucagon synthesis was never detected indicating that the α-cell population was absent. Magnification is 200×.

FIG. 7 (FIGS. 7a, 7b). Analysis of amylase expression in exocrine tissues newborn pancreas of +/− and −/− Pax6 deficient mice.

Amylase expression in the exocrine tissue remained unaffected in −/− mice.

FIG. 8 (FIGS. 8a, 8b, 8c, 8d). Analysis of β-galactosidase, insulin, glucagon and Pdx1 expression in newborn pancreases of mice homozygous for both Pax6 and Pax4.

Few β-galactosidase positive cells were observed in mice lacking both Pax4 and Pax6 (a, b). These cells expressed neither insulin (a) or glucagon (b). However, Pdx1 positive cells could be detected in the pancreas. Magnification panels a, b is 200×; c, d is 400×.

Figure 9:
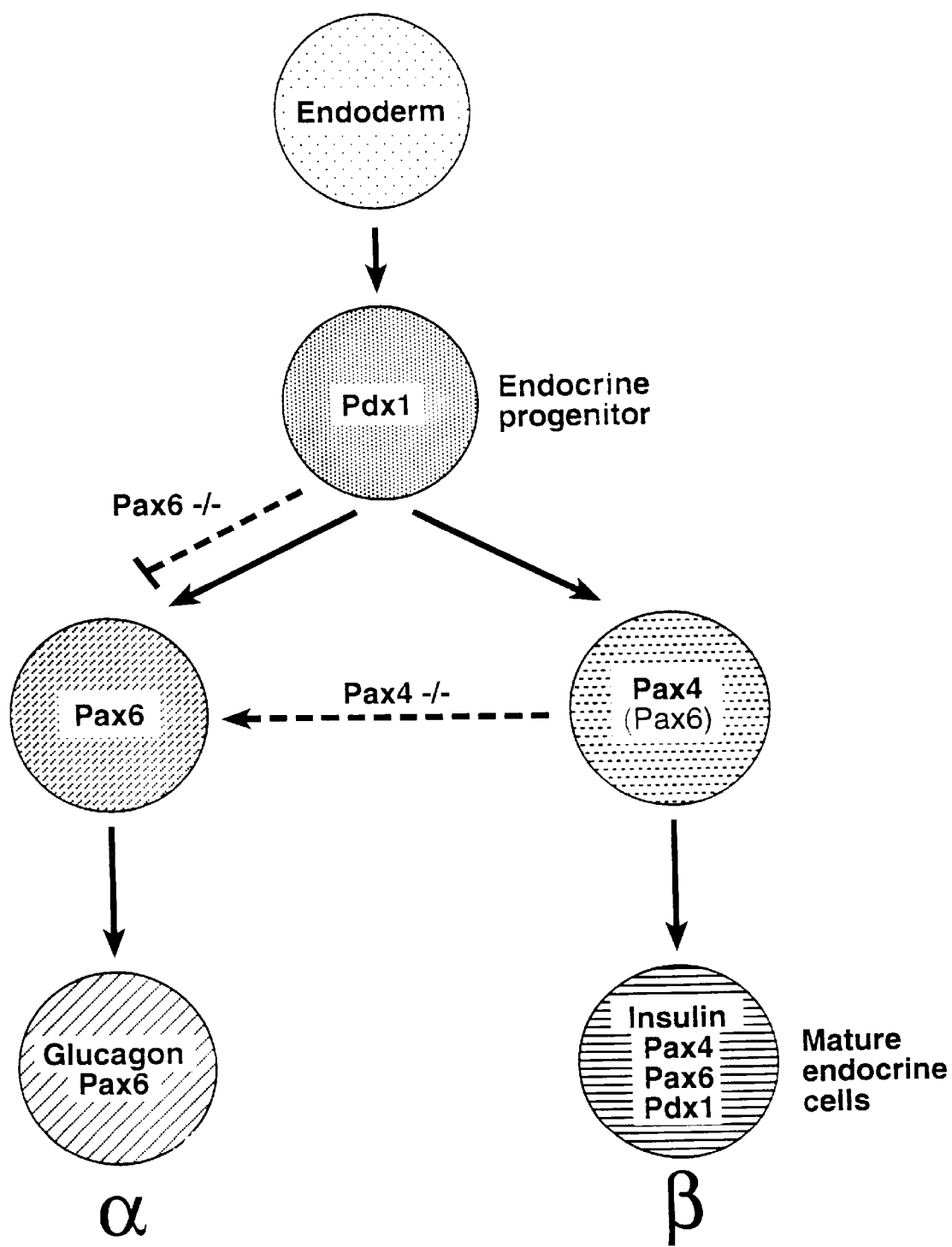

FIG. 9. Proposed model for the role of Pax4 and Pax6 during differentiation of α- and β-cells during pancreatic development.

At day 8.5 p.c., Pdx1 expression define the region of the endoderm that will give rise to the exocrine and endocrine progenitor cells. The onset of Pax gene expression in the endocrine progenitor at day 9.0 p.c. defines these cells into two types of precursors. Precursors expressing both Pax4 and Pax6 will develop into mature insulin-producing β-cells while precursors expressing only Pax6 differentiate into glucagon-producing α-cells. Deletion of Pax4 diverts the β-cell lineage into the α-cell lineage. Absence of Pax6 eliminates the lineage for α-cells.

FIGS. 10 to 17. Sequences 1 to 4 (identified below by SEQ ID No.).

A better understanding of the present invention and of its many advantages will be had from the following examples, given by way of illustration.

EXAMPLES

Antibodies used against insulin, glucagon and amylase are commercially available from several companies. The antibodies used in Applicants' experiments were purchased from Boehringer Mannheim. The Pdx1 antibody was a generous gift from Prof. Thomas Edlund (Department of Microbiology, University of Umea, S-901 87 Umea, Sweden). Antibodies with the same specificity i.e. which specifically recognize the Pdx1 protein can be prepared using the Pdx1 protein as an antigen according to conventional procedures.

Example 1

Preparation of construct for homologous recombination and generation of Pax6-deficient mice Pax6-deficient mice were generated by homologous recombination in embryonic stem (ES) cells using well established techniques; for example, A. L. Joyner, Editor, "Gene targeting: a practical approach", Oxford University Press, Oxford, 1993. Briefly, an 11.5 kb genomic DNA fragment was isolated from a 129Sv mouse genomic library by homology screening using for probe a fragment of the Pax6 cDNA describe by Walter and Gruss, Development 113 (1993), 1435–1449). Production of genomic library, homology screening and all cloning steps were done using techniques well known in the art; see, for example, Sambrook et al., "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985. The Pax6 initiation codon and the entire paired domain were replaced by inserting a β-galactosidase-neomycin cassette into the BamHI-KpnI restriction site of the genomic DNA thus creating a mutation that eliminates any functional Pax6 protein (FIG. 1). The targeting construct was then introduced into the embryonic stem cell line R1 (Nagy, A., et al., Proc. Natl. Acad. Sci. U.S.A. 90 (1993), 8424–8428). Approximately 107 ES cells in a tris-phosphate buffer solution containing 30 ug of linearized targeting construct was electroporated with a single pulse of 500 uF/250 volt at room temperature. Cells were then plated and selected against the antibiotic G418 for two weeks. Resistant clones were individually isolated and their DNA was digested with the restriction enzymes SpeI-EcoRV and analysed by Southern blot using a probe specific for the Pax6 locus. Mutated Pax6 allele generated a 8.2 kb fragment compared to a 11 kb fragment wild type alleles. Out of 200 colonies analysed, 3 were found to contains a mutated Pax6 allele. Chimeric animals were produce by aggregating ES cells of a mutant clone to 8 cell morula embryos from the NMRI mouse line. Chimeric animals were then mated for germline transmission.

Example 2

Expression of Pax6 in developing and newborn animals.

β-galactosidase activity was analysed in heterozygous embryos during development. Embryos were isolated at different stages of development and fixed 30 minutes in 2% formaldehyde/0.02% glutaraldehyde in phosphate-buffered saline (PBS) and stained overnight at 30° C. in a PBS solution containing 0.1% X-gal, 2 mM $MgCl_2$, 5 mM $K_3Fe(CN)_6$, 5 mM $K_4Fe(CN)_6$, 0.2% Nonidet P-40 and 2.5 mM deoxycholic acid. Pax6/β-galactosidase staining was first detected in the open neural plate and closed neural fold of day 8.0 embryos (FIG. 2). A few hours later at day 8.5, strong β-galactosidase staining was observed in the prospective forebrain and hindbrain and progressed caudaly has the neural tube closed. No expression was detected in the prospective midbrain region. At day 9.5, the forebrain divides into the telencephalon, diencephalon and the optic vesicle forms. Strong β-galactosidase activity was also detected in the hindbrain, neural tube and developing pancreas. Expression was maintained in the brain, eye, neural tube and pancreas throughout development and persisted in some cells of the adult animal. β-galactosidase expression corresponded with the Pax6 expression pattern previously described by in situ analyses (Walter and Gruss, Development 113 (1991), 1435–1449). Applicants did not detect any ectopic β-galactosidase expression in mutant animals.

Homozygous animals lacked eye and nasal bulb which resulted in craniofacial malformations (FIG. 3). They also had defects in the dien- and telencephalon and died a few minutes after birth. The phenotypes observed in homozygous Pax6-LacZ mice were similar to the ones described in homozygous Small eye mutants (Stoykova, A., et al., Development 122 (1996), 3453–3465; Grindley, J. C., et al., Development 121 (1995),1433–1442).

Example 3

Expression of Pax6 in endocrine cells of pancreas

Pax6 Expression was analysed in developing pancreas by studying β-galactosidase activity in heterozygous Pax6-LacZ embryos. β-galactosidase positive cells were first detected in discrete cells of the pancreatic bulge at day 9.0 p.c. Pax6 expression was maintained in a subset of cells during pancreatic development and became restricted to the islets of Langerhans in newborn and adult animals (FIG. 4). No Pax6 expression was detected in the exocrine tissue.

Figure 5A:
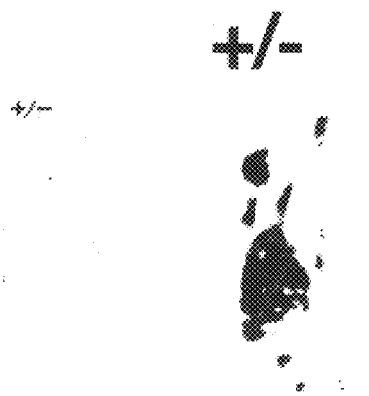

Hormonal production in embryonic and newborn pancreas was verified by indirect immunochemistry using a monoclonal antibody specific for insulin or glucagon (FIGS. 5a, b, c). Cells expressing PaxG synthesized either glucagon or insulin indicating that Pax6 is expressed in both α- and β-cells. Pancreases were isolated and stained for β-galactosidase activity as describe above. After staining, tissues were embedded in paraffin and 10 um sections were performed. All Immunohistochemistry analysis on paraffin sections were accomplished after β-galactosidase staining according to standard procedure. Briefly, sections were rehydrated in a series of ethanol dilutions and prehybridyzed in a blocking solution containing 1 mg/ml blocking reagent (Boehringer Mannheim cat.# 1096176), 20% foetal calf serum, 100 mM maleic acid, 150 mM NaCl for 30 minutes at room temperature in a humid box. The blocking solution was removed and sections were then hybridised overnight in a humid box at room temperature with a primary antibody against glucagon or insulin. Both primary antibodies were obtained from Sigma (Cat# G-2654; I-2018) and diluted 1:500 in blocking buffer. Sections were then washed 3 times 10 minutes in a TBST buffer containing 10 mM Tris-Cl pH 8.0, 150 mM NaCl, 0.05% Tween-20 and hybridised overnight with a secondary anti-mouse-IgG antibody couple to horse radish peroxydase (Cappel Teknika Corp. antibody cat.# 55559). Sections were again washed 3 times in TBST buffer and stained in a TBST solution containing 0.5 mg/ml diaminobenzidine, 0.066% $H_2O_2$.

Example 4

Figure 5D:
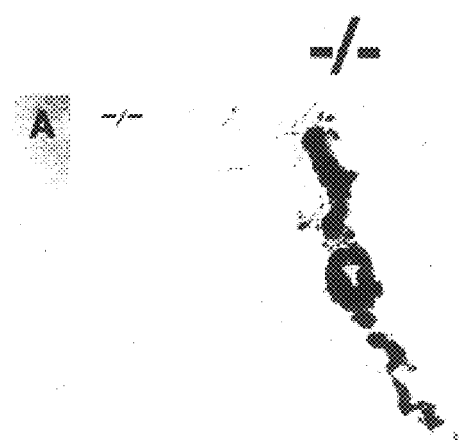
Figure 5B:
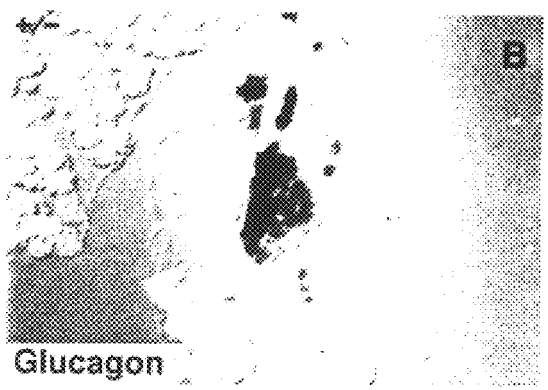
Figure 5E:
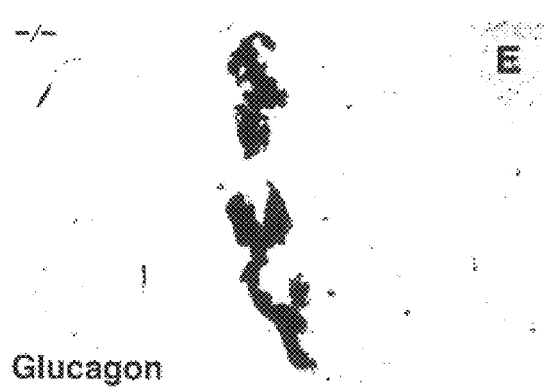
Figure 5C:
Figure 5F:
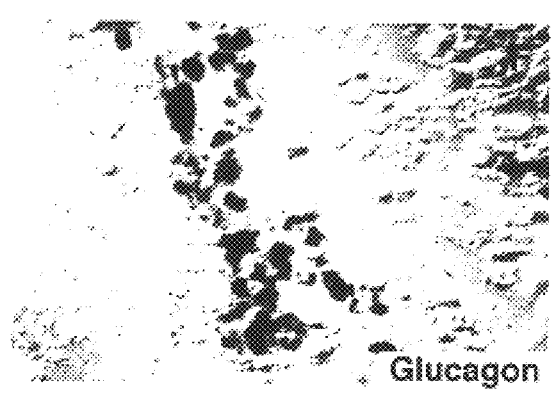
Figure 8A:
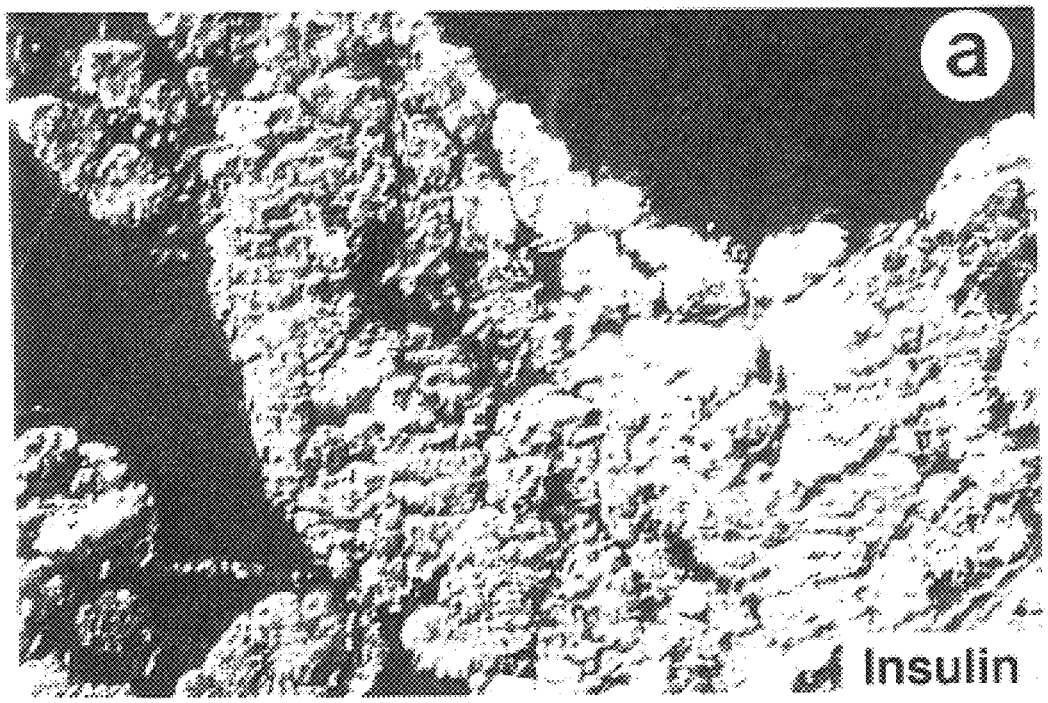
Figure 8B:
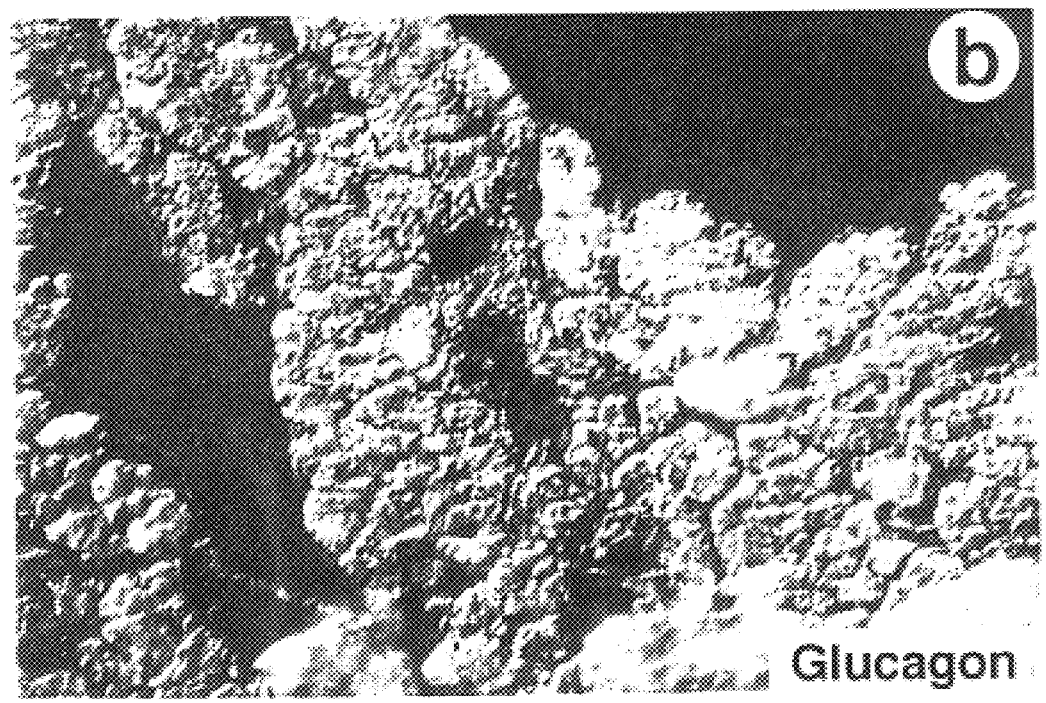
Figure 8C:
Figure 8D:

Analysis of insulin and glucagon in mice lacking the Pax6 gene.

β-galactosidase positive cells were still detected in the pancreas of homozygous Pax6 mutant newborn animals. However, they failed to form islets and remained scattered throughout the exocrine tissue (FIGS. 5d, e, f). Furthermore, β-galactosidase positive cells produced only insulin. Glucagon-producing cells were never detected indicating that the α-cells population was absent in homozygous mutant pancreas. Similar results were obtained with the natural mouse mutant Small eye (FIG. 6) which also contains a mutated Pax6 alleles (Van de Meer-Jong, R., et al., Genomics 7 (1990), 270–275).

Furthermore, although the β-cell population in pancreas of homozygous mutant Pax6 mice still produced insulin, they did not form islets of Langerhans. In normal pancreas, the formation of islets is not clonal by origin (Deltour, L., et al., Development 112 (1991), 1115–1121) but is thought to be the result of cell migration and aggregation occurring late in development (Herrera, P. L., et al., Development 113 (1991), 1257–1265). It is possible that Pax6 may be involved in organising the endocrine cells into islets. Recent studies suggest that cell adhesion molecules play an important role in forming islets (Dahl, U., et al., Development 122 (1996), 2895–2902; Moller, C. J., et al., Mol. Endocrinol. 6 (1992), 1332–1342; Rouiller, D. G., et al., Dev. Biol. 148 (1991), 233–242) and it has been shown that Pax6 can bind to the promoter of at least one cell adhesion molecule (Chalepakis, G., et al., DNA Cell Biol. 13 (1994), 891–900). Finally, the exocrine tissue of homozygous pancreas was compared to heterozygous pancreas for amylase production (Sigma antibody cat.# A-8273). No difference was observed between homozygous and heterozygous indicating that the exocrine tissue was unaffected in the absence of Pax6 (FIG. 7).

Example 5

Both Pax4 and Pax6 are required for differentiation of endocrine

Since the Pax4 gene is required for β-cells differentiation because mutant mice do not develop insulin-secreting cells. The fate of endocrine cells in the pancreas of newborn animals lacking both Pax6 and Pax4 was analysed. A small population of β-galactosidase positive cells was still observed within the exocrine tissue. While cells did not produce any insulin or glucagon, expression of the homeobox gene Pdx1 could be detected (FIG. 8). Since Pdx1 is expressed only in precursor cells and mature β-cells (Guz, Y., et al., Development 121 (1995), 11–18) and homozygous Pax4 mice lacking β-cells do not express Pdx1, Applicants' results suggest that the endocrine precursor cells remained present in the pancreas of Pax4/Pax6 homozygous newborn mice but failed to differentiate into mature endocrine cells.

Based on Applicants' observations, Applicants propose that Pax4 and Pax6 determine the cell fate of the endocrine progenitor during development (FIG. 9). In a first step, the Pdx1 gene defines the region of the endoderm that will give rise to pancreatic exocrine and endocrine progenitors since its expression occurs before expression of Pax genes (Serup, P., et al., Biochem. J. 310 (1995), 997–1003; Guz, Y., et al., Development 121 (1995), 11–18) and mice lacking Pdx1 do not form a pancreas (Jonsson, J., et al., Nature 371 (1994), 606–609). The onset of Pax expression in the pancreas divides endocrine progenitors into two populations: cells expressing both Pax4 and Pax6 differentiate into mature β-cells while cells expressing only Pax6 differentiate into α-cells. Absence of Pax4 diverts all progenitors into the α-cell lineage since Pax6 remains present in these cells. This is supported by the observation that homozygous Pax4 mutant mice while lacking β-cells, have a larger than normal α-cell population. Deletion of Pax6 eliminates the α-cells lineage altogether or may divert progenitors to the β-cells lineage. When both Pax4 and Pax6 are absent, progenitors fail to develop into mature endocrine cells. Thus both Pax genes are required for endocrine cell differentiation during pancreatic development.

Having thus described in detail preferred embodiments of the present invention, it is to be understood that the invention defined by the appended claims is not to be limited by particular details set forth in the above description as many apparent variations thereof are possible without departing from the spirit or scope thereof.

---

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 2481 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "oligonucleotide"

(ix) FEATURE:
      (A) NAME/KEY: CDS
      (B) LOCATION:163..1470

(xi) SEQUENCE DESCRIPTION: SEQ ID NO: 1:

```
ACAACGACGA AAGAGAGGAT GCCTCTTAAA GGCAGAAGAC TTTAACCAAG GGCGGTGAGC        60

AGATGTGTGA GATCTTCTAT TCTAGAAGTG GACGTATATC CCAGTTCTCA GAGCCCCGTA       120

TTCGAGCCCC GTGGGATCCG GAGGCTGCCA ACCAGCTCCA GC ATG CAG AAC AGT         174
                                                 Met Gln Asn Ser
                                                   1

CAC AGC GGA GTG AAT CAG CTT GGT GGT GTC TTT GTC AAC GGG CGG CCA         222
His Ser Gly Val Asn Gln Leu Gly Gly Val Phe Val Asn Gly Arg Pro
  5                  10                  15                  20

CTG CCG GAC TCC ACC CGG CAG AAG ATC GTA GAG CTA GCT CAC AGC GGG         270
Leu Pro Asp Ser Thr Arg Gln Lys Ile Val Glu Leu Ala His Ser Gly
                 25                  30                  35

GCC CGG CCG TGC GAC ATT TCC CGA ATT CTG CAG ACC CAT GCA GAT GCA         318
Ala Arg Pro Cys Asp Ile Ser Arg Ile Leu Gln Thr His Ala Asp Ala
             40                  45                  50

AAA GTC CAG GTG CTG GAC AAT GAA AAC GTA TCC AAC GGT TGT GTG AGT         366
Lys Val Gln Val Leu Asp Asn Glu Asn Val Ser Asn Gly Cys Val Ser
 55                  60                  65

AAA ATT CTG GGC AGG TAT TAC GAG ACT GGC TCC ATC AGA CCC AGG GCA         414
Lys Ile Leu Gly Arg Tyr Tyr Glu Thr Gly Ser Ile Arg Pro Arg Ala
     70                  75                  80

ATC GGA GGG AGT AAG CCA AGA GTG GCG ACT CCA GAA GTT GTA AGC AAA         462
Ile Gly Gly Ser Lys Pro Arg Val Ala Thr Pro Glu Val Val Ser Lys
 85                  90                  95                 100

ATA GCC CAG TAT AAA CGG GAG TGC CCT TCC ATC TTT GCT TGG GAA ATC         510
Ile Ala Gln Tyr Lys Arg Glu Cys Pro Ser Ile Phe Ala Trp Glu Ile
                105                 110                 115

CGA GAC AGA TTA TTA TCC GAG GGG GTC TGT ACC AAC GAT AAC ATA CCC         558
Arg Asp Arg Leu Leu Ser Glu Gly Val Cys Thr Asn Asp Asn Ile Pro
            120                 125                 130

AGT GTG TCA TCA ATA AAC AGA GTT CTT CGC AAC CTG GCT AGC GAA AAG         606
Ser Val Ser Ser Ile Asn Arg Val Leu Arg Asn Leu Ala Ser Glu Lys
        135                 140                 145
```

| | | | | | | | | | | | | | | | |
|---|---|---|---|---|---|---|---|---|---|---|---|---|---|---|---|
| CAA | CAG | ATG | GGC | GCA | GAC | GGC | ATG | TAT | GAT | AAA | CTA | AGG | ATG | TTG | AAC | 654 |
| Gln | Gln | Met | Gly | Ala | Asp | Gly | Met | Tyr | Asp | Lys | Leu | Arg | Met | Leu | Asn |
| 150 | | | | | 155 | | | | | 160 | | | | |

```
CAA CAG ATG GGC GCA GAC GGC ATG TAT GAT AAA CTA AGG ATG TTG AAC      654
Gln Gln Met Gly Ala Asp Gly Met Tyr Asp Lys Leu Arg Met Leu Asn
150                 155                 160

GGG CAG ACC GGA AGC TGG GGC ACA CGC CCT GGT TGG TAT CCC GGG ACT      702
Gly Gln Thr Gly Ser Trp Gly Thr Arg Pro Gly Trp Tyr Pro Gly Thr
165                 170                 175                 180

TCA GTA CCA GGG CAA CCC ACG CAA GAT GGC TGC CAG CAA CAG GAA GGA      750
Ser Val Pro Gly Gln Pro Thr Gln Asp Gly Cys Gln Gln Gln Glu Gly
                185                 190                 195

GGG GGA GAG AAC ACC AAC TCC ATC AGT TCT AAC GGA GAA GAC TCG GAT      798
Gly Gly Glu Asn Thr Asn Ser Ile Ser Ser Asn Gly Glu Asp Ser Asp
            200                 205                 210

GAA GCT CAG ATG CGA CTT CAG CTG AAG CGG AAG CTG CAA AGA AAT AGA      846
Glu Ala Gln Met Arg Leu Gln Leu Lys Arg Lys Leu Gln Arg Asn Arg
                215                 220                 225

ACA TCT TTT ACC CAA GAG CAG ATT GAG GCT CTG GAG AAA GAG TTT GAG      894
Thr Ser Phe Thr Gln Glu Gln Ile Glu Ala Leu Glu Lys Glu Phe Glu
230                 235                 240

AGG ACC CAT TAT CCA GAT GTG TTT GCC CGG GAA AGA CTA GCA GCC AAA      942
Arg Thr His Tyr Pro Asp Val Phe Ala Arg Glu Arg Leu Ala Ala Lys
245                 250                 255                 260

ATA GAT CTA CCT GAA GCA AGA ATA CAG GTA TGG TTT TCT AAT CGA AGG      990
Ile Asp Leu Pro Glu Ala Arg Ile Gln Val Trp Phe Ser Asn Arg Arg
                265                 270                 275

GCC AAA TGG AGA AGA GAA GAG AAA CTG AGG AAC CAG AGA AGA CAG GCC     1038
Ala Lys Trp Arg Arg Glu Glu Lys Leu Arg Asn Gln Arg Arg Gln Ala
            280                 285                 290

AGC AAC ACT CCT AGT CAC ATT CCT ATC AGC AGC AGC TTC AGT ACC AGT     1086
Ser Asn Thr Pro Ser His Ile Pro Ile Ser Ser Ser Phe Ser Thr Ser
                295                 300                 305

GTC TAC CAG CCA ATC CCA CAG CCC ACC ACA CCT GTC TCC TCC TTC ACA     1134
Val Tyr Gln Pro Ile Pro Gln Pro Thr Thr Pro Val Ser Ser Phe Thr
310                 315                 320

TCA GGT TCC ATG TTG GGC CGA ACA GAC ACC GCC CTC ACC AAC ACG TAC     1182
Ser Gly Ser Met Leu Gly Arg Thr Asp Thr Ala Leu Thr Asn Thr Tyr
325                 330                 335                 340

AGT GCT TTG CCA CCC ATG CCC AGC TTC ACC ATG GCA AAC AAC CTG CCT     1230
Ser Ala Leu Pro Pro Met Pro Ser Phe Thr Met Ala Asn Asn Leu Pro
                345                 350                 355

ATG CAA CCC CCA GTC CCC AGT CAG ACC TCC TCA TAC TCG TGC ATG CTG     1278
Met Gln Pro Pro Val Pro Ser Gln Thr Ser Ser Tyr Ser Cys Met Leu
                360                 365                 370

CCC ACC AGC CCG TCA GTG AAT GGG CGG AGT TAT GAT ACC TAC ACC CCT     1326
Pro Thr Ser Pro Ser Val Asn Gly Arg Ser Tyr Asp Thr Tyr Thr Pro
            375                 380                 385

CCG CAC ATG CAA ACA CAC ATG AAC AGT CAG CCC ATG GGC ACC TCG GGG     1374
Pro His Met Gln Thr His Met Asn Ser Gln Pro Met Gly Thr Ser Gly
                390                 395                 400

ACC ACT TCA ACA GGA CTC ATT TCA CCT GGA GTG TCA GTT CCC GTC CAA     1422
Thr Thr Ser Thr Gly Leu Ile Ser Pro Gly Val Ser Val Pro Val Gln
405                 410                 415                 420

GTT CCC GGG AGT GAA CCT GAC ATG TCT CAG TAC TGG CCT CGA TTA CAG     1470
Val Pro Gly Ser Glu Pro Asp Met Ser Gln Tyr Trp Pro Arg Leu Gln
                425                 430                 435

TAAAGAGAGA AGGAGAGAGC ATGTGATCGA GAGAGGAAAT TGTGTTCACT CTGCCAATGA   1530

CTATGTGGAC ACAGCAGTTG GGTATTCAGG AAAGAAAGAG AAATGGCGGT TAGAAGCACT   1590

TCACTTTGTA ACTGTCCTGA ACTGGAGCCC GGGAATGGAC TAGAACCAAG GACCTTGCGT   1650

ACAGAAGGCA CGGTATCAGT TGGAACAAAT CTTCATTTTG GTATCCAAAC TTTTATTCAT   1710
```

```
TTTGGTGTAT TATTTGTAAA TGGGCATTGG TATGTTATAA TGAAGAAAAG AACAACACAG    1770

GCTGTTGGAT CGCGGATCTG TGTTGCTCAT GTGGTTGTTT AAAGGAAACC ATGATCGACA    1830

AGATTTGCCA TGGATTTAAG AGTTTTATCA AGATATATCA AATACTTCTC CCCATCTGTT    1890

CATAGTTTAT GGACTGATGT TCCAAGTTTG TATCATTCCT TTGCATATAA TTGAACCTGG    1950

GACAACACAC ACTAGATATA TGTAAAAACT ATCTGTTGGT TTTCCAAAGG TTGTTAACAG    2010

ATGAAGTTTA TGTGCAAAAA AGGGTAAGAT ATGAATTCAA GGAGAAGTTG ATAGCTAAAA    2070

GGTAGAGTGT GTCTTCGATA TAATACAATT TGTTTTATGT CAAAATGTAA GTATTTGTCT    2130

TCCCTAGAAA TCCTCAGAAT GATTTCTATA ATAAAGTTAA TTTCATTTAT ATTTGACAAG    2190

AATACTCTAT AGATGTTTTA TACACATTTT CATGCAATCA TTTGTTTCTT TCTTGGCCAG    2250

CAAAAGTTAA TTGTTCTTAG ATATAGCTGT ATTACTGTTC ACAGTCCAAT CATTTTGTGC    2310

ATCTAGAATT CATTCCTAAT CAATTAAAAG TGCTTGCAAG AGTTTTAAAC CTAAGTGTTT    2370

TGCAGTTGTT CACAAATACA TATCAAAATT AACCATTGTT GATTGTAAAA AAAAAACCAT    2430

GCCAAAGCCT TTGTATTTTC TTTATTACCC TTGACCGTAA GACATGAATT C             2481
```

(2) INFORMATION FOR SEQ ID NO: 2:

(i) SEQUENCE CHARACTERISTICS:
        (A) LENGTH: 436 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Gln Asn Ser His Ser Gly Val Asn Gln Leu Gly Gly Val Phe Val
 1               5                  10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Thr
        35                  40                  45

His Ala Asp Ala Lys Val Gln Val Leu Asp Asn Glu Asn Val Ser Asn
    50                  55                  60

Gly Cys Val Ser Lys Ile Leu Gly Arg Tyr Tyr Glu Thr Gly Ser Ile
 65                  70                  75                  80

Arg Pro Arg Ala Ile Gly Gly Ser Lys Pro Arg Val Ala Thr Pro Glu
                85                  90                  95

Val Val Ser Lys Ile Ala Gln Tyr Lys Arg Glu Cys Pro Ser Ile Phe
           100                 105                 110

Ala Trp Glu Ile Arg Asp Arg Leu Leu Ser Glu Gly Val Cys Thr Asn
       115                 120                 125

Asp Asn Ile Pro Ser Val Ser Ser Ile Asn Arg Val Leu Arg Asn Leu
   130                 135                 140

Ala Ser Glu Lys Gln Gln Met Gly Ala Asp Gly Met Tyr Asp Lys Leu
145                 150                 155                 160

Arg Met Leu Asn Gly Gln Thr Gly Ser Trp Gly Thr Arg Pro Gly Trp
               165                 170                 175

Tyr Pro Gly Thr Ser Val Pro Gly Gln Pro Thr Gln Asp Gly Cys Gln
           180                 185                 190
```

```
Gln Gln Glu Gly Gly Gly Glu Asn Thr Asn Ser Ile Ser Ser Asn Gly
        195                 200                 205
Glu Asp Ser Asp Glu Ala Gln Met Arg Leu Gln Leu Lys Arg Lys Leu
    210                 215                 220
Gln Arg Asn Arg Thr Ser Phe Thr Gln Glu Gln Ile Glu Ala Leu Glu
225                 230                 235                 240
Lys Glu Phe Glu Arg Thr His Tyr Pro Asp Val Phe Ala Arg Glu Arg
                245                 250                 255
Leu Ala Ala Lys Ile Asp Leu Pro Glu Ala Arg Ile Gln Val Trp Phe
            260                 265                 270
Ser Asn Arg Arg Ala Lys Trp Arg Arg Glu Glu Lys Leu Arg Asn Gln
        275                 280                 285
Arg Arg Gln Ala Ser Asn Thr Pro Ser His Ile Pro Ile Ser Ser Ser
    290                 295                 300
Phe Ser Thr Ser Val Tyr Gln Pro Ile Pro Gln Pro Thr Thr Pro Val
305                 310                 315                 320
Ser Ser Phe Thr Ser Gly Ser Met Leu Gly Arg Thr Asp Thr Ala Leu
                325                 330                 335
Thr Asn Thr Tyr Ser Ala Leu Pro Pro Met Pro Ser Phe Thr Met Ala
            340                 345                 350
Asn Asn Leu Pro Met Gln Pro Pro Val Pro Ser Gln Thr Ser Ser Tyr
        355                 360                 365
Ser Cys Met Leu Pro Thr Ser Pro Ser Val Asn Gly Arg Ser Tyr Asp
370                 375                 380
Thr Tyr Thr Pro Pro His Met Gln Thr His Met Asn Ser Gln Pro Met
385                 390                 395                 400
Gly Thr Ser Gly Thr Thr Ser Thr Gly Leu Ile Ser Pro Gly Val Ser
                405                 410                 415
Val Pro Val Gln Val Pro Gly Ser Glu Pro Asp Met Ser Gln Tyr Trp
            420                 425                 430
Pro Arg Leu Gln
        435

(2) INFORMATION FOR SEQ ID NO: 3:

(i) SEQUENCE CHARACTERISTICS:
        (A) LENGTH: 1275 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(ix) FEATURE:
        (A) NAME/KEY: CDS
        (B) LOCATION:166..1161

(xi) SEQUENCE DESCRIPTION: SEQ ID NO: 3:

ACCAGCAACC CTGGAGCCTG CACAGACCCT GAGACCTCTT CCTGAATTCC CACCTTTTTT      60

CCTCCATCCA GTACCAGTCC CAAAGAGAAA CTTCCAGAAG GAGCTCTCCG TTTTCAGTTT     120

GCCAGTTGGC TTCCTGTCCT TCTGCGAGGA GTACCAGTGT GAAGC ATG CAG CAG         174
                                                Met Gln Gln
                                                  1

GAC GGA CTC AGC AGT GTG AAT CAG CTA GGG GGA CTC TTT GTG AAT GGC       222
Asp Gly Leu Ser Ser Val Asn Gln Leu Gly Gly Leu Phe Val Asn Gly
  5                  10                  15
```

| | | |
|---|---|---|
| CGG CCC CTT CCT CTG GAC ACC AGG CAG CAG ATT GTG CAG CTA GCA ATA<br>Arg Pro Leu Pro Leu Asp Thr Arg Gln Gln Ile Val Gln Leu Ala Ile<br>20                     25                    30                 35 | 270 |
| AGA GGG ATG CGA CCC TGT GAC ATT TCA CGG AGC CTT AAG GTA TCT AAT<br>Arg Gly Met Arg Pro Cys Asp Ile Ser Arg Ser Leu Lys Val Ser Asn<br>              40                    45                    50 | 318 |
| GGC TGT GTG AGC AAG ATC CTA GGA CGC TAC TAC CGC ACA GGT GTC TTG<br>Gly Cys Val Ser Lys Ile Leu Gly Arg Tyr Tyr Arg Thr Gly Val Leu<br>                  55                    60                    65 | 366 |
| GAA CCC AAG TGT ATT GGG GGA AGC AAA CCA CGT CTG GCC ACA CCT GCT<br>Glu Pro Lys Cys Ile Gly Gly Ser Lys Pro Arg Leu Ala Thr Pro Ala<br>70                     75                    80 | 414 |
| GTG GTG GCT CGA ATT GCC CAG CTA AAG GAT GAG TAC CCT GCT CTT TTT<br>Val Val Ala Arg Ile Ala Gln Leu Lys Asp Glu Tyr Pro Ala Leu Phe<br>        85                    90                    95 | 462 |
| GCC TGG GAG ATC CAA CAC CAG CTT TGC ACT GAA GGG CTT TGT ACC CAG<br>Ala Trp Glu Ile Gln His Gln Leu Cys Thr Glu Gly Leu Cys Thr Gln<br>100                   105                 110              115 | 510 |
| GAC AAG GCT CCC AGT GTG TCC TCT ATC AAT CGA GTA CTT CGG GCA CTT<br>Asp Lys Ala Pro Ser Val Ser Ser Ile Asn Arg Val Leu Arg Ala Leu<br>                 120                 125              130 | 558 |
| CAG GAA GAC CAG AGC TTG CAC TGG ACT CAA CTC AGA TCA CCA GCT GTG<br>Gln Glu Asp Gln Ser Leu His Trp Thr Gln Leu Arg Ser Pro Ala Val<br>            135                 140                145 | 606 |
| TTG GCT CCA GTT CTT CCC AGT CCC CAC AGT AAC TGT GGG GCT CCC CGA<br>Leu Ala Pro Val Leu Pro Ser Pro His Ser Asn Cys Gly Ala Pro Arg<br>150                   155                 160 | 654 |
| GGC CCC CAC CCA GGA ACC AGC CAC AGG AAT CGG GCT ATC TTC TCC CCG<br>Gly Pro His Pro Gly Thr Ser His Arg Asn Arg Ala Ile Phe Ser Pro<br>            165                 170                175 | 702 |
| GGA CAA GCC GAG GCA CTG GAG AAA GAG TTT CAG CGT GGG CAG TAT CCA<br>Gly Gln Ala Glu Ala Leu Glu Lys Glu Phe Gln Arg Gly Gln Tyr Pro<br>180                   185                 190              195 | 750 |
| GAT TCA GTG GCC CGT GGG AAG CTG GCT GCT GCC ACC TCT CTG CCT GAA<br>Asp Ser Val Ala Arg Gly Lys Leu Ala Ala Ala Thr Ser Leu Pro Glu<br>                 200                 205              210 | 798 |
| GAC ACG GTG AGG GTT TGG TTT TCT AAC AGA AGA GCC AAA TGG CGC AGG<br>Asp Thr Val Arg Val Trp Phe Ser Asn Arg Arg Ala Lys Trp Arg Arg<br>            215                 220                225 | 846 |
| CAA GAG AAG CTG AAA TGG GAA GCA CAG CTG CCA GGT GCT TCC CAG GAC<br>Gln Glu Lys Leu Lys Trp Glu Ala Gln Leu Pro Gly Ala Ser Gln Asp<br>230                   235                 240 | 894 |
| CTG ACG ATA CCA AAA AAT TCT CCA GGG ATC ATC TCT GCA CAG CAG TCC<br>Leu Thr Ile Pro Lys Asn Ser Pro Gly Ile Ile Ser Ala Gln Gln Ser<br>245                   250                 255 | 942 |
| CCC GGC AGT GTA CCC TCA GCT GCC TTG CCT GTG CTG GAA CCA TTG AGT<br>Pro Gly Ser Val Pro Ser Ala Ala Leu Pro Val Leu Glu Pro Leu Ser<br>260                   265                 270              275 | 990 |
| CCT TCC TTC TGT CAG CTA TGC TGT GGG ACA GCA CCA GGC AGA TGT TCC<br>Pro Ser Phe Cys Gln Leu Cys Cys Gly Thr Ala Pro Gly Arg Cys Ser<br>            280                 285                290 | 1038 |
| AGT GAC ACC TCA TCC CAG GCC TAT CTC CAA CCC TAC TGG GAC TGC CAA<br>Ser Asp Thr Ser Ser Gln Ala Tyr Leu Gln Pro Tyr Trp Asp Cys Gln<br>                 295                 300              305 | 1086 |
| TCC CTC CTT CCT GTG GCT TCC TCC TCA TAT GTG GAA TTT GCC TGC CCT<br>Ser Leu Leu Pro Val Ala Ser Ser Ser Tyr Val Glu Phe Ala Cys Pro<br>310                   315                 320 | 1134 |
| GCC TCA CCA CCC ATC CTG TGC ATC ATC TGATTGGAGG CCCAGGACAA<br>Ala Ser Pro Pro Ile Leu Cys Ile Ile<br>325                   330 | 1181 |

```
GTGCCATCAT CCCATTGCTC AAACTGGCCA TAAGACACCT CTATTTGACA GTAATAAAAA      1241

CCTTTTCTTA GATGTTAAAA AAAAAAAAGG GGGG                                 1275
```

(2) INFORMATION FOR SEQ ID NO: 4:

(i) SEQUENCE CHARACTERISTICS:
        (A) LENGTH: 332 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Gln Gln Asp Gly Leu Ser Ser Val Asn Gln Leu Gly Gly Leu Phe
 1               5                  10                  15

Val Asn Gly Arg Pro Leu Pro Leu Asp Thr Arg Gln Gln Ile Val Gln
             20                  25                  30

Leu Ala Ile Arg Gly Met Arg Pro Cys Asp Ile Ser Arg Ser Leu Lys
         35                  40                  45

Val Ser Asn Gly Cys Val Ser Lys Ile Leu Gly Arg Tyr Tyr Arg Thr
     50                  55                  60

Gly Val Leu Glu Pro Lys Cys Ile Gly Gly Ser Lys Pro Arg Leu Ala
65                  70                  75                  80

Thr Pro Ala Val Val Ala Arg Ile Ala Gln Leu Lys Asp Glu Tyr Pro
                 85                  90                  95

Ala Leu Phe Ala Trp Glu Ile Gln His Gln Leu Cys Thr Glu Gly Leu
            100                 105                 110

Cys Thr Gln Asp Lys Ala Pro Ser Val Ser Ser Ile Asn Arg Val Leu
        115                 120                 125

Arg Ala Leu Gln Glu Asp Gln Ser Leu His Trp Thr Gln Leu Arg Ser
    130                 135                 140

Pro Ala Val Leu Ala Pro Val Leu Pro Ser Pro His Ser Asn Cys Gly
145                 150                 155                 160

Ala Pro Arg Gly Pro His Pro Gly Thr Ser His Arg Asn Arg Ala Ile
                165                 170                 175

Phe Ser Pro Gly Gln Ala Glu Ala Leu Glu Lys Glu Phe Gln Arg Gly
            180                 185                 190

Gln Tyr Pro Asp Ser Val Ala Arg Gly Lys Leu Ala Ala Ala Thr Ser
        195                 200                 205

Leu Pro Glu Asp Thr Val Arg Val Trp Phe Ser Asn Arg Arg Ala Lys
    210                 215                 220

Trp Arg Arg Gln Glu Lys Leu Lys Trp Glu Ala Gln Leu Pro Gly Ala
225                 230                 235                 240

Ser Gln Asp Leu Thr Ile Pro Lys Asn Ser Pro Gly Ile Ile Ser Ala
                245                 250                 255

Gln Gln Ser Pro Gly Ser Val Pro Ser Ala Ala Leu Pro Val Leu Glu
            260                 265                 270

Pro Leu Ser Pro Ser Phe Cys Gln Leu Cys Cys Gly Thr Ala Pro Gly
        275                 280                 285

Arg Cys Ser Ser Asp Thr Ser Ser Gln Ala Tyr Leu Gln Pro Tyr Trp
    290                 295                 300

Asp Cys Gln Ser Leu Leu Pro Val Ala Ser Ser Ser Tyr Val Glu Phe
305                 310                 315                 320

Ala Cys Pro Ala Ser Pro Pro Ile Leu Cys Ile Ile
                325                 330
```

What is claimed is:

1. A composition comprising a nucleic acid sequence encoding a functional and expressible Pax6 protein and a second nucleic acid sequence encoding a functional and expressible Pax4 protein.

2. The composition of claim 1, wherein the nucleic acid sequence encoding the Pax6 protein is operatively linked to regulatory elements for the expression and/or targeting of the Pax6 protein to specific cells, and the nucleic acid sequence encoding the Pax4 protein is operatively linked to regulatory elements for expression and/or targeting of the Pax4 protein to specific cells.

3. A composition comprising a nucleic acid sequence encoding Pax6 protein operatively linked to regulatory elements for expression of the Pax6 protein in pancreatic cells.

4. An in vitro pancreatic cell comprising an exogenous nucleic acid sequence encoding Pax6 protein operatively linked to regulatory elements for expression of Pax6 in the cell.

* * * * *